(12) United States Patent
Seeberger et al.

(10) Patent No.: US 8,536,153 B2
(45) Date of Patent: Sep. 17, 2013

(54) **CHEMICAL SYNTHESIS OF PHOSPHATIDYLINOSITOL MANNOSIDE GLYCANS FROM *MYCOBACTERIUM TUBERCULOSIS***

(75) Inventors: Peter H. Seeberger, Kleinmachnow (DE); Siwarutt Boonyarattanakalin, Pathum Thani (TH); Bernd Lepenies, Berlin (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/127,320

(22) PCT Filed: Nov. 3, 2009

(86) PCT No.: PCT/EP2009/007845
§ 371 (c)(1),
(2), (4) Date: Jun. 23, 2011

(87) PCT Pub. No.: WO2010/051961
PCT Pub. Date: May 14, 2010

(65) Prior Publication Data
US 2011/0256173 A1    Oct. 20, 2011

(30) Foreign Application Priority Data
Nov. 4, 2008   (EP) .................................. 08019264

(51) Int. Cl.
| A61K 31/715 | (2006.01) |
| A61K 31/70 | (2006.01) |
| A61K 31/7028 | (2006.01) |
| A61K 31/7034 | (2006.01) |
| C07H 15/207 | (2006.01) |

(52) U.S. Cl.
USPC ................ 514/54; 514/25; 514/35; 536/17.6; 536/17.1; 536/123.1; 424/197.11; 530/395

(58) Field of Classification Search
USPC ..................... 514/54, 25, 35; 536/17.6, 17.1; 536/123.1; 424/197.11; 530/395
See application file for complete search history.

(56) References Cited

U.S. PATENT DOCUMENTS
2006/0147476 A1* 7/2006 Schofield .................... 424/268.1

FOREIGN PATENT DOCUMENTS
WO     9912562 A1   3/1999

OTHER PUBLICATIONS

Boonyarattanakalin et al., "Chemical synthesis of all phosphatidylinositol mannoside (PIM) glycans from *Mycobacterium tuberculosis*." J Am Chem Soc. Dec. 10, 2008;130(49):16791-9.
De Libero et al., "Recognition of lipid antigens by T cells." Nat Rev Immunol. Jun. 2005;5(6):485-96.
Elie et al., "Synthesis of 1-O-(1,2-Di-O-palmitoyl-SN-glycero-3-phosphoryl)-2-O-α-D-mannopyranosyl-D-MYO-inositol: a fragment of mycobacterial phospholipids" Tetrahedron vol. 45, Issue 11, 1989, pp. 3477-3486.
Hoppe et al., "Identification of phosphatidylinositol mannoside as a mycobacterial adhesin mediating both direct and opsonic binding to nonphagocytic mammalian cells." Infect Immun. Sep. 1997;65(9):3896-905.
Liu et al., "Total synthesis of phosphatidylinositol mannosides of *Mycobacterium tuberculosis*." J Am Chem Soc. Mar. 22, 2006;128(11):3638-48.
Martín, "The dream of a vaccine against tuberculosis; new vaccines improving or replacing BCG?" Eur Respir J. Jul. 2005;26(1):162-7.
Ravidà et al., "Synthesis of glycosyl phosphates from 1,2-orthoesters and application to in situ glycosylation reactions." Org Lett. Apr. 27, 2006;8(9):1815-8.
Rojas et al., "Phosphatidylinositol mannoside from *Mycobacterium tuberculosis* binds alpha5beta1 integrin (VLA-5) on CD4+ T cells and induces adhesion to fibronectin." J Immunol. Sep. 1, 2006;177(5):2959-68.
Sacchettini et al., "Drugs versus bugs: in pursuit of the persistent predator *Mycobacterium tuberculosis*." Nat Rev Microbiol. Jan. 2008;6(1):41-52.
Torrelles et al., "Fine discrimination in the recognition of individual species of phosphatidyl-myo-inositol mannosides from *Mycobacterium tuberculosis* by C-type lectin pattern recognition receptors." J Immunol. Aug. 1, 2006;177(3):1805-16.
Zhaozhong et al., "Ready routes to key myo-inositol component of GPIs employing microbial arene oxidation or Ferrier reaction." J. Chem. Soc., Perkin Trans. 1, 1998, 631-632.
International Search Report for PCT/EP2009/007845.

* cited by examiner

*Primary Examiner* — Shaojia Anna Jiang
*Assistant Examiner* — Michael C Henry
(74) *Attorney, Agent, or Firm* — Caesar, Rivise, Bernstein, Cohen & Pokotilow, Ltd.

(57) ABSTRACT

The efficient synthesis of phosphatidylinositol mono- to hexa-mannoside ($PIM_1$ to $PIM_6$) is reported. The invention relates to these phosphatidylinositol mono- to hexa-mannosides carrying a linker and a reactive functional group, e.g. the sulfhydryl group, a protein, a fluorescent probe, or a solid phase. The invention further relates to vaccines comprising the PIMs linked to a carrier protein or an antigen.

13 Claims, 5 Drawing Sheets

A

B

CHEMICAL SYNTHESIS OF PHOSPHATIDYLINOSITOL MANNOSIDE GLYCANS FROM *MYCOBACTERIUM TUBERCULOSIS*

FIELD OF THE INVENTION

The invention relates to phosphatidylinositol mannoside (PIM) glycans carrying a reactive functional group, a carrier protein, a fluorescent probe, an antigen or a solid phase, and to a vaccine containing such PIMs carrying an antigen.

BACKGROUND OF THE INVENTION

Tuberculosis (TB) is a complex disease and a major cause of mortality world-wide. Despite the development of new treatments, TB remains a global health concern. Annually, there are more than seven million new cases and two million deaths caused by TB (C. Martin, Eur Respir J 2005, 26:162-167). Coinfection with HIV leads to an exacerbation of the disease and contributes to higher mortality in HIV patients. Programs to combat TB in many countries have failed to eradicate TB, partly due to the spread of multidrug-resistant TB and the low efficacy of the BCG vaccine. Therefore, the exploration of novel drug targets and vaccines against *Mycobacterium tuberculosis* (Mtb), the main causative pathogen of TB, is essential.

Among pathogenic bacteria, Mtb causes more deaths in humans than any other pathogen. Approximately one third of the world population has already been infected by Mtb. Mtb is an intracellular pathogen that has evolved to persist efficiently in infected macrophages. The composition of the Mtb cell wall is important for the interaction with host cells during the initial steps of the infection. Later, cell wall components play a crucial role in modulating the pro-inflammatory response by macrophages and also serve as a protective barrier to prevent anti-tuberculosis agents from permeating inside. Consequently, the antibiotics used for the treatment of tuberculosis require long term administration (J. C. Sacchettini, E. J. Rubin and J. S. Freundlich, Nat Rev Microbiol 2008, 6:41-52). Mortality in people living in developing countries is high since their access to these antibiotics is often limited and compliance with treatment courses is low.

The major components of the mycobacterial cell wall are the mycoyl arabinogalactan-peptidoglycan (mAGP) complex and interspersed glycolipids including ManLAM, LAM, LM, and PIMs. While the mAGP complex is covalently attached to the bacterial plasma membrane, the glycolipids are non-covalently attached through their phosphatidyl-myo-inositol (PI) anchor. PIMs constitute the only conserved substructure of LM, LAM and ManLAM (FIG. 1). The inositol residue of PI is mannosylated at the C-2 position to form $PIM_1$ and further at the C-6 position to form $PIM_2$, one of the two most abundant naturally occurring PIMs, along with $PIM_6$. Further α-1,6 mannosylations give rise to $PIM_3$ and $PIM_4$, the common biosynthetic precursors for $PIM_5$, $PIM_6$ and the much larger LM structures. LAM is constituted by attachment of arabinans—the repeating units of α-1,5 arabinose terminated with a single β-1,2 arabinose—to unknown mannose units of LM. The non-reducing end arabinose in the arabinan moiety of LAM can be capped at the C-5 position with one or two α-mannose units to furnish ManLAM.

Among the surface components involved in the Mtb interaction with host cells, PIMs play a crucial role in the modulation of the host immune response. The functional importance of PIMs was emphasized by the finding that PIMs bind to receptors on both phagocytic (J. B. Torrelles et al., J. Immunol. 2006, 177:1805-1816) and nonphagocytic (H. C. Hoppe et al., Infect Immun 1997, 65:3896-3905) mammalian cells. Recently, it has been shown that PIMs, but neither LAM nor ManLAM interact with the VLA-5 on $CD4^+T$ lymphocytes and induce the activation of this integrin (R. E. Rojas et al., J Immunol 2006, 177:2959-2968). These findings suggest that PIMs are not only secreted to the extracellular environment, but also exposed on the surface of Mtb to interact with host cells.

Although different functions have been ascribed to the PIMs, it remains to be determined whether and to which extent the different PIM substructures display biological activity. A better understanding of the mycobacterial cell wall biosynthesis is required to be able to counteract with the problems of drug resistance and bacterial persistence. Synthetic PIMs represent important biochemical tools to elucidate biosynthetic pathways and to reveal interactions with receptors on host cells. PIMs are potential vaccine antigens and/or adjuvants.

Several synthetic PIMs containing fewer mannoside units have been synthesized employing various chemical methodologies. In contrast to $PIM_3$ and $PIM_4$ that contain only α-1,6 mannosidic linkages, $PIM_5$ and $PIM_6$ also incorporate α-1,2 mannosides that might contribute to different biological activities of these PIMs. None of the studies to date utilized synthetic PIMs that contain linkers for immobilization. Coupling of synthetic PIMs to carrier proteins, beads, quantum dots, microarray or surface plasmon resonance (SPR) surfaces opens a host of options for biochemical studies.

SUMMARY OF THE INVENTION

The invention relates to a compound of formula (I)

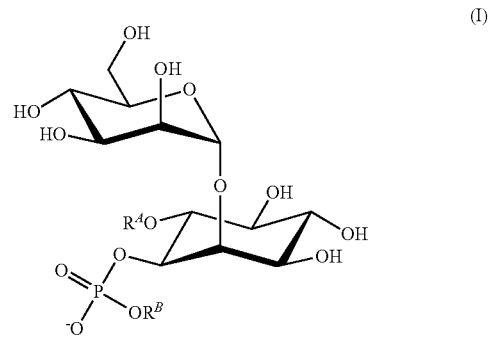

(I)

wherein
$R^A$ is H, a mannoside, di-mannoside, tri-mannoside, tetra-mannoside or penta-mannoside of formula (II), (III), (IV), (V) or (VI) below, respectively; and
$R^B$ is $-(CH_2)_n-X$ wherein n is between 2 and 10 or $-(CH_2CH_2O)_mCH_2CH_2X$ wherein m is between 1 and 5, and X is a reactive functional group, a carrier protein, a fluorescent probe, an antigen or a solid phase.

The invention further relates to vaccines comprising a compound of formula (I) wherein X is a carrier protein or an antigen.

4: KLH+CpG

5: KLH-PIM$_6$ (covalent)

The experimental procedure is described below under the title "Immunization of mice and detection of anti-KLH antibody levels in sera".

FIG. 3A, B:

Immunization was performed as described below under the title "Immunization of mice and detection of anti-KLH antibody levels in sera". Levels of anti-KLH antibody subclasses (anti-KLH IgG1 and IgG2a) in sera of immunized mice were measured by ELISA. Meaning of 1, 2, 3, 4, 5, 6 see FIG. 2.

FIG. 4:

Mice were immunized as described below under the title "Immunization of mice and detection of anti-KLH antibody levels in sera". On day 20, spleens were removed and splenocytes were isolated as described below under the title "T cell proliferation and ELISpot analysis". The results are expressed as a stimulation index (SI) which is the net proliferation of lymphocyte cultures stimulated with KLH divided by the net proliferation of lymphocyte cultures in medium.

Figure 1:
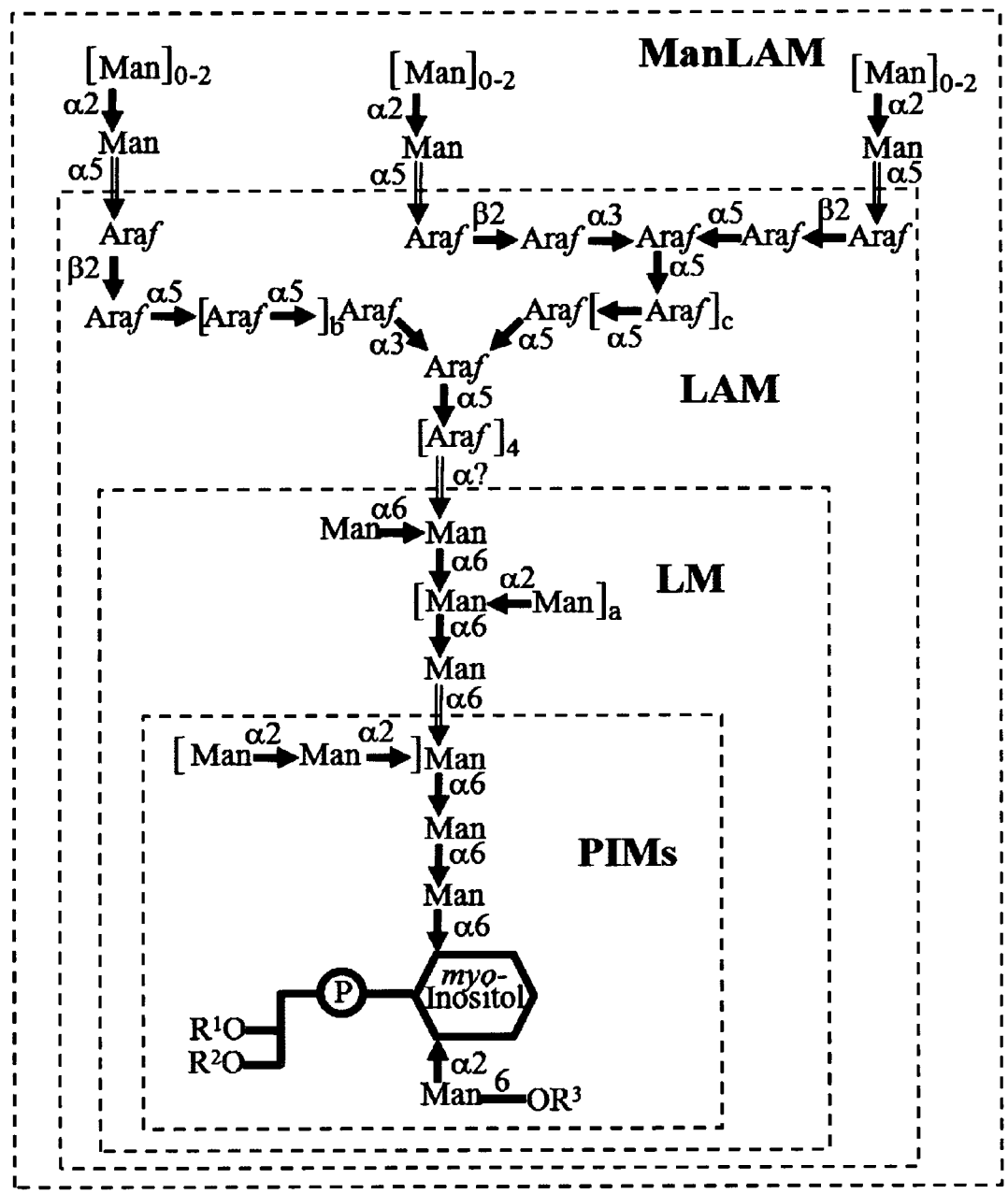
FIG. 1. Structural features of PIMs, LM, LAM and ManLAM of *Mycobacterium tuberculosis*. PIMs are the common precursors of more complex components of the mycobacterial cell wall including lipomannan (LM), lipo-arabinomannan (LAM), and mannan capped lipo-arabinomannan (ManLAM). (a, b, and c are varied; typically, $R^2$ is tuberculostearic acid, $R^1$ and $R^3$ are various fatty acids.)
Figure 2:
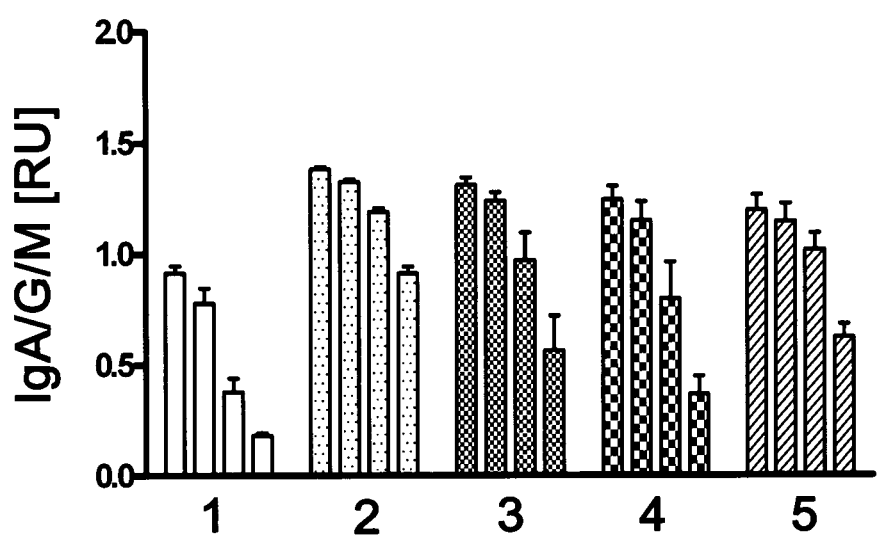
FIG. 2:
1: KLH alone
2: KLH+Freund's adjuvant
3: KLH+Alum

Meaning of 1, 2, 3, 4, 5, 6 see FIG. 2.

FIG. 5:

Mice were immunized as described below under the title "Immunization of mice and detection of anti-KLH antibody levels in sera". On day 20, spleens were removed and splenocytes were isolated as described below under the title "T cell proliferation and ELISpot analysis". The results are expressed as spot forming units (sfu) which is the number of IFN-γ producing cells per total cells ($2\times10^5$). Dashed lines represent number of IFN-γ spots measured when splenocytes from unimmunized mice were stimulated with ConA or KLH.

Meaning of 1, 2, 3, 4, 5, 6 see FIG. 2.

DETAILED DESCRIPTION OF THE INVENTION

The invention relates to a compound of formula (I)

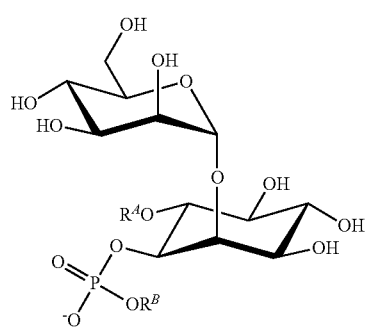

(I)

wherein $R^A$ is H, a residue of formula (II), (III), (IV), (V) or (VI)

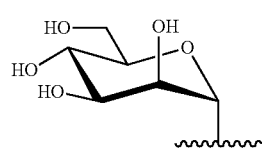

(II)

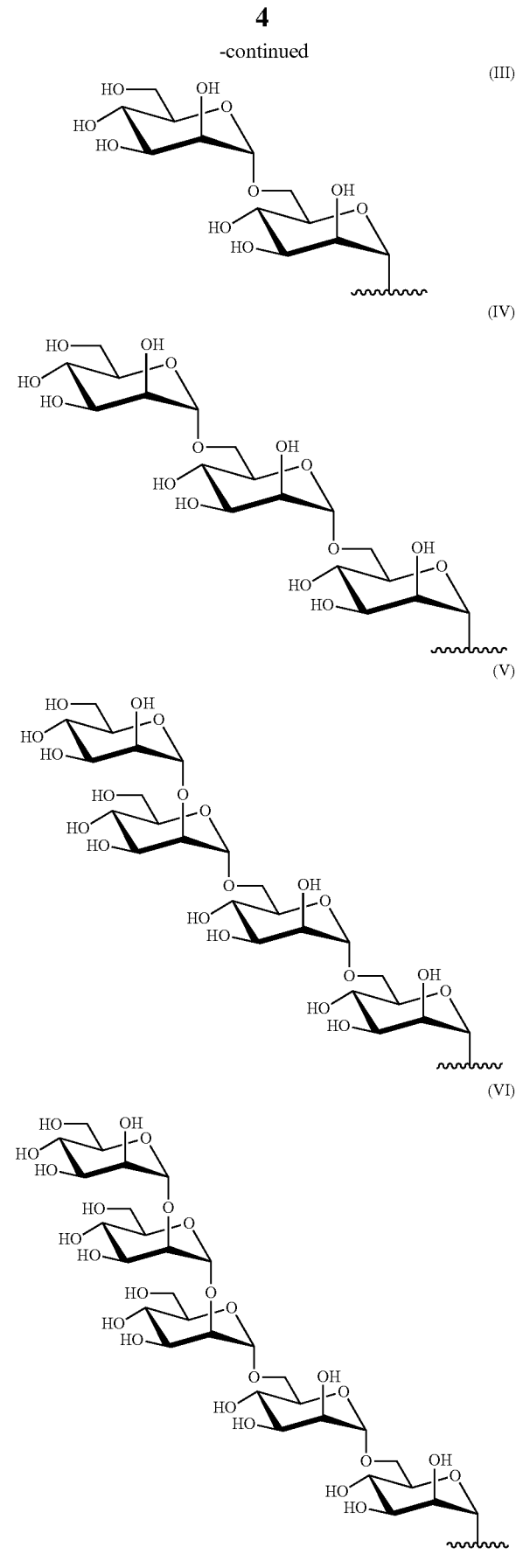

and $R^B$ is —$(CH_2)_n$—X wherein n is between 2 and 10 or —$(CH_2CH_2O)_mCH_2CH_2X$ wherein m is between 1 and 5, and X is a reactive functional group, a protein, a fluorescent probe or a solid phase.

The compound of formula (I) wherein $R^A$ is H is called $PIM_1$. The compound of formula (I) wherein $R^A$ is a residue of formula (II) is called $PIM_2$. The compound of formula (I) wherein $R^A$ is a residue of formula (III) is called $PIM_3$. The compound of formula (I) wherein $R^A$ is a residue of formula (IV) is called $PIM_4$. The compound of formula (I) wherein $R^A$ is a residue of formula (V) is called $PIM_5$. The compound of formula (I) wherein $R^A$ is a residue of formula (VI) is called $PIM_6$.

The native diacylglycerol phosphate at the C-1 position of myo-inositol is replaced by the residue $R^B$ connected to the phosphate residue.

In $R^B$ with the meaning —$(CH_2)_n$—X, n is between 2 and 10, preferably between 3 and 8, for example 3, 4, 5, 6 or 7, preferably 4, 5 or 6, most preferably 6.

In $R^B$ with the meaning —$(CH_2CH_2O)_mCH_2CH_2X$, m is between 1 and 5, preferably 1, 2 or 3, in particular 2.

X as a reactive functional group is a functional group suitable for coupling the PIM compound to a protein (including a proteinaceous antigen), to a fluorescent probe or to a solid phase. A preferred example of a reactive functional group is the sulfhydryl group (—SH), which can be reacted with a protein, a fluorescent probe or a solid phase carrying a maleimido function, which then leads to a thiosuccinimido group. Another preferred reactive group is a maleimido function of formula (VII)

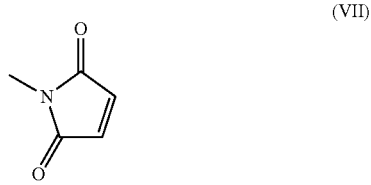

(VII)

which can be reacted with a protein, a fluorescent probe or a solid phase carrying a sulfhydryl function again resulting in a thiosuccinimido group. A further suitable reactive function is an amino group, which can be reacted with a protein, a fluorescent probe or a solid phase carrying an optionally activated carboxyl group. The carboxyl may be activated by any of the standard activating reagent used for amide bond formation as is widely known in peptide chemistry, for example as a 1-hydroxybenztriazole or N-hydroxysuccinimide ester. The corresponding optionally activated carboxy group is another suitable reactive functional group X, which then may react with an amine function in a protein, a fluorescent probe or a solid phase.

X as a protein is preferably a carrier protein useful in a vaccine. Examples of carrier proteins are bovine serum albumin (BSA), ovalbumin (OVA), keyhole limpet hemocyanin (KLH), thyroglobulin, and tetanus toxoid. Preferred carrier proteins are KLH and OVA. X with the meaning protein may further comprise functional groups linking the protein to the alkylene group or polyethyleneoxy group defined in $R^B$, preferably a thiosuccinimido group obtained on reaction of a sulfhydryl function —SH with a maleimido function of formula (VII), or an amide function obtained on reaction of an amine with an activated carboxyl function.

An antigen X may be any useful antigen considered to be used in a vaccine. Usually this antigen is not antigenic enough to give rise to an immunogenic response of a host when injected into the host, but may elicit such a reaction after conjugation to a PIM as defined under formula (I). Examples of antigens considered are keyhole limpet hemocyanin (KLH), HBs antigen (from hepatitis B virus, HBV), pertussis, diphtheria and tetanus toxoid antigen, and surface antigens of pathogens with low immunogenicity, such as malaria, schistosomiasis, or HIV. In principle all proteins from bacteria, viruses, parasites or fungi can be considered as suitable antigens. As is described above for X as a carrier protein, X with the meaning antigen may further comprise functional groups linking the antigen to the alkylene group or polyethyleneoxy group defined in $R^B$.

A fluorescent probe X considered for conjugation to PIMs is, for example, fluorescein, Texas red, Tokyo green, Pennsylvania green, rhodamines, Cy5, Cy3, green fluorescent protein, BFP, mTFP1, emerald, citrine, mOrange, mApple, mCherry, mGrape and other fluorophores, and also fluorescent nanocrystals. A fluorescent probe X may further comprise functional groups linking the antigen to the alkylene group or polyethyleneoxy group defined in $R^B$, for example a thiosuccinimido function or an amido function as explained above.

A solid phase X may be a standard solid material used for sugars and proteins, e.g. a glass slide, plastic slide or beads made of silica, alox or other suitable carrier materials further comprising a suitable functional group connecting the solid phase to the alkylene group or polyethyleneoxy group defined in $R^B$, for example a thiosuccinimido function or an amido function as explained above.

Preferred are compounds of formula (I) wherein, $R^A$ is a residue of formula (I), (II), (III), (IV), (V) or (VI), $R^B$ is —$(CH_2)_n$—X wherein n is between 2 and 10, and X is a reactive functional group. Most preferred are the compounds of the following formula designated $PIM_1$, $PIM_2$, $PIM_3$, $PIM_4$, $PIM_5$ and $PIM_6$, wherein $R^B$ is —$(CH_2)_6$—SH, in particular the compounds $PIM_2$ and $PIM_6$.

$PIM_1$

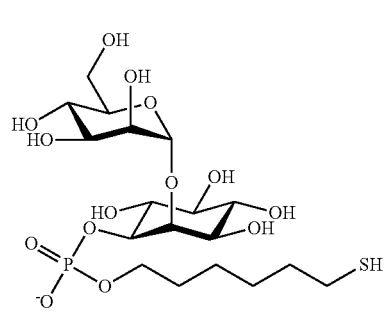

$PIM_2$

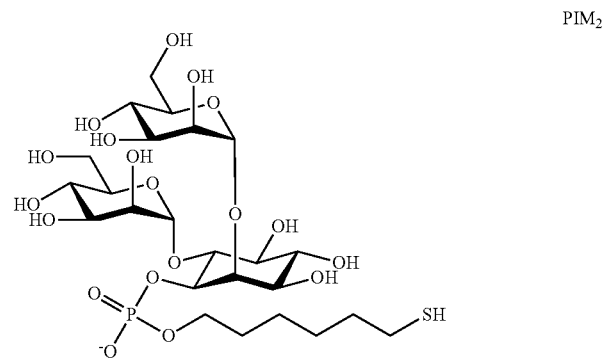

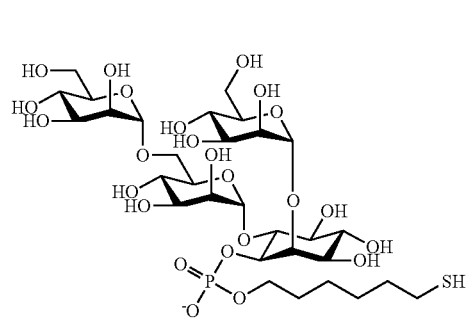
PIM₃
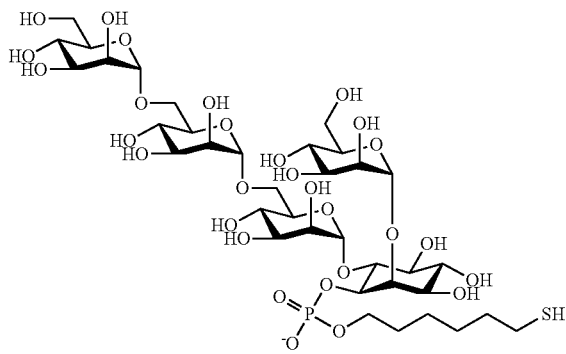
PIM₄
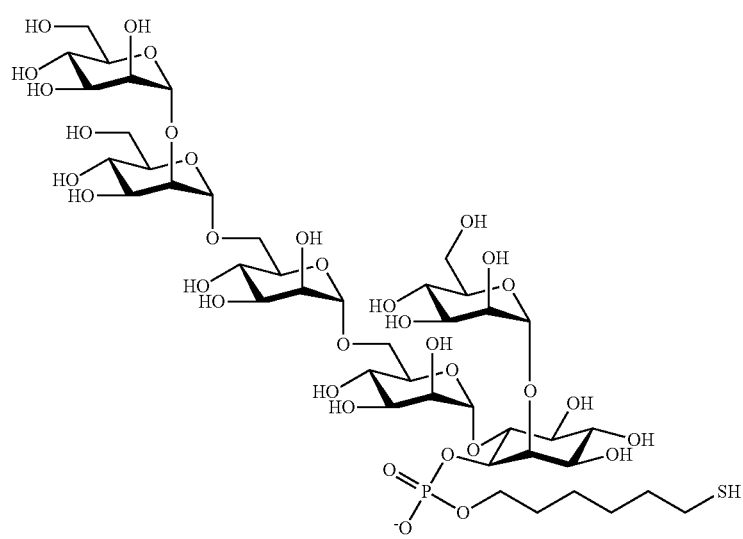
PIM₅
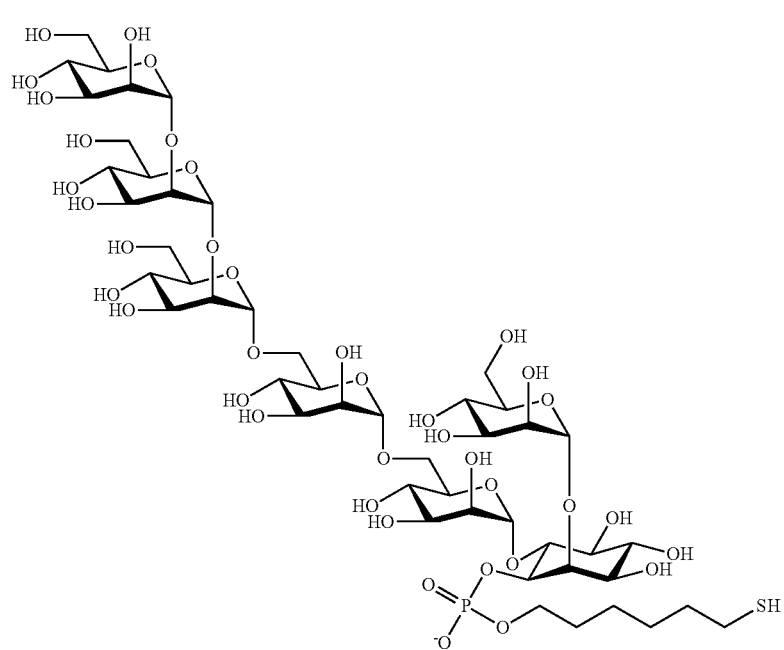
PIM₆

The invention further relates to vaccines comprising a compound of formula (I) wherein X is a carrier protein or an antigen. Preferred vaccines wherein the PIMs act as adjuvants are conjugates with antigens selected from HBs, pertussis, diphtheria, tetanus toxoid, malaria, schistosomiasis, and HIV antigens. In principle all vaccines consisting of protein antigens from bacteria, viruses, parasites or fungi can be considered as suitable.

Retrosynthetic analysis. The overall structure of the synthetic PIM targets of formula (I) can be attained by the convergent union of oligomannosides with D-myo-inositol containing pseudosaccharides and a residue $R^B$, e.g. the thiol-terminated phosphate linker (Scheme 1). Late-stage couplings between protected oligosaccharide fragments (1-4) and 8 allow for parallel syntheses of the intermediates for all target molecules. The key glycosylations in these syntheses are the couplings between mannosyl phosphate 1, oligomannosyl trichloroacetimidates (2-4) and the common pseudotrisaccharide 8. The two main carbohydrate moieties are coupled, followed by protecting group manipulations. Subsequently, a phosphate diester linker is installed using an H-phosphonate followed by oxidation of phosphorus. Since the preferred target molecules contain sulfur in the residue $R^B$ that is known to deactivate the Pd/C catalyst, the permanent benzyl protecting groups are globally removed via Birch reduction.

The stereoselectivity of each glycosydic bond formation is ensured by neighboring C-2 acyl participating groups. Anomeric dibutyl phosphate ester was employed as a leaving group for the mannose building blocks that can be readily prepared. This method proved advantageous when compared to previous PIM syntheses. Three mannose building blocks (1, 5, and 10) are needed in addition to the inositol building block.

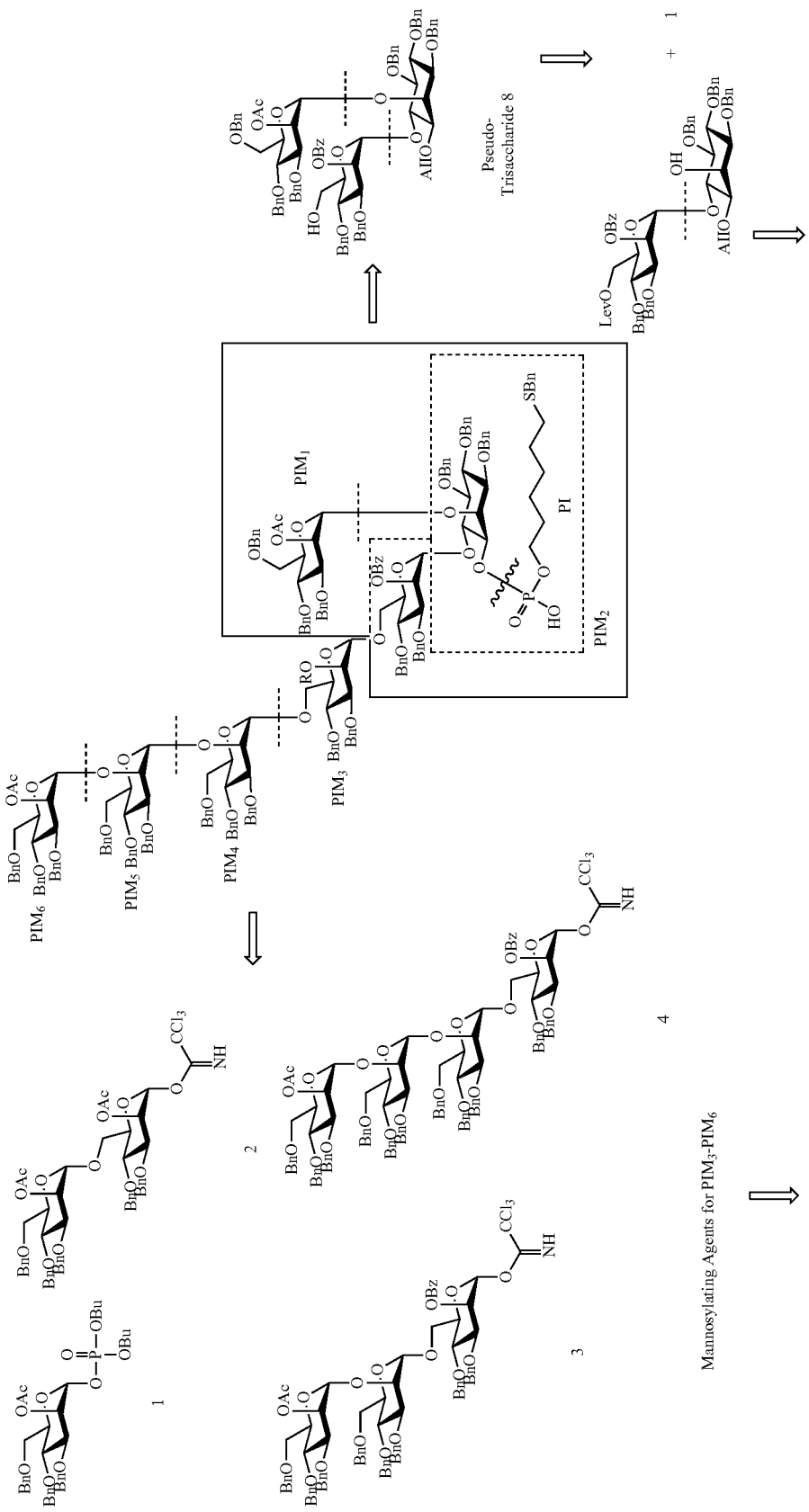

-continued
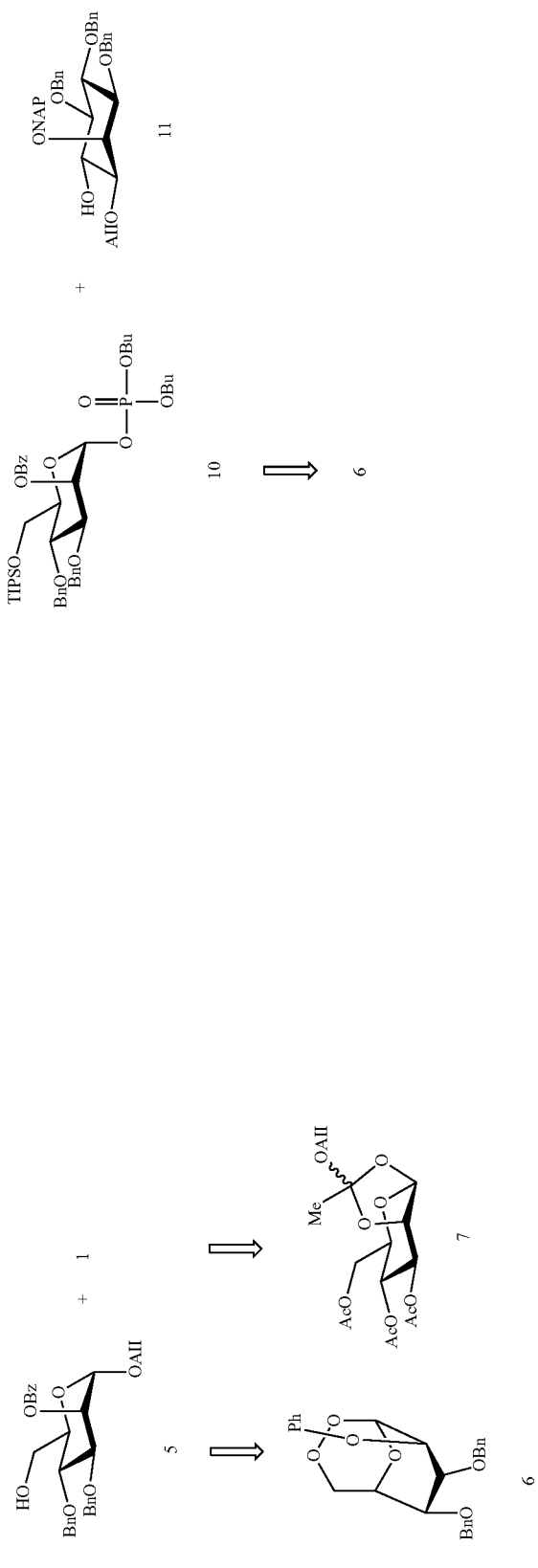
R = Bz or Ac
----- = Phosphate Glycosylations
∿∿∿ = H-phosphorylations

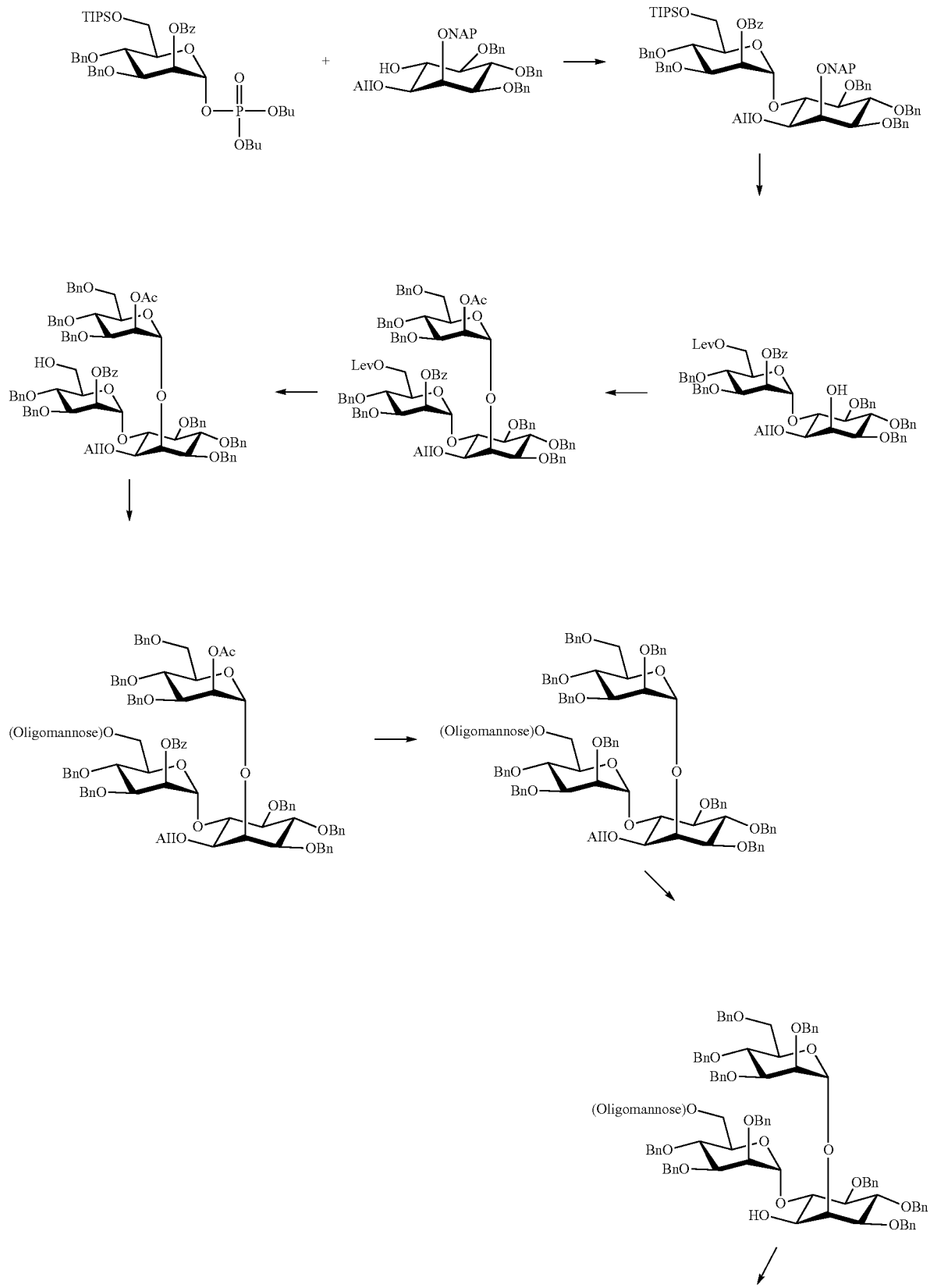
Scheme 2. Synthesis of PIMs

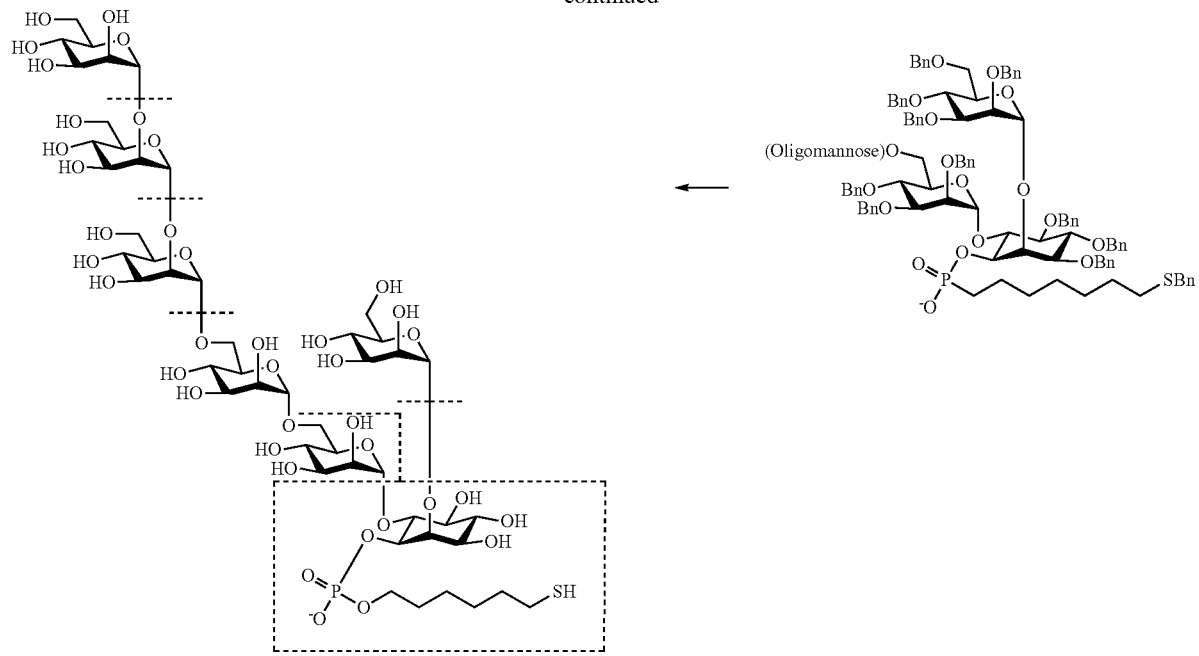

Syntheses of Monosaccharide Building Blocks.

Mannosyl building blocks 1, 5, and 10 were synthesized from mannose bicyclic and tricyclic orthoesters (6, 12) (A. Ravida et al., Org Letters 2006, 8:1815-1818). Starting from O-mannose, mannosyl phosphate 1 was accessed in six steps by dibutyl phosphoric acid opening of the bicyclic orthoester 7. Mannosyl tricyclic orthoester 6 is readily available from D-mannose over six high yielding steps. This process required only one purification at the last step and gave 6 in 70% overall yield. The versatile intermediate 6 was opened by allyl alcohol upon activation with $BF_3 \cdot Et_2O$ to afford 5 in excellent yield. Treatment of orthoester 6 with dibutyl phosphate selectively opened the tricyclic orthoester to furnish glycosyl phosphate 13, leaving the C-6 hydroxyl group unprotected. The installation of a triisopropylsilyl (TIPS) group was straightforward and furnished building block 10.

Reagents and conditions: (a) i. $Ac_2O$, $HClO_4$ (cat.), ii. HBr/HOAc, iii. MeOH, Lutidine, 90%, three steps; (b) i. NaOMe/MeOH/THF, ii. NaH, BnBr, DMF, quant. two steps; (c) $HOP(O)(OBu)_2$, 4 Å MS 93%; (d) i. BzCl, Py, ii. HBr/HOAc, iii. AllOH, Lutidine, iv. NaOMe/MeOH/THF, reflux, v. CSA, MeCN, vi. NaH, BnBr, DMF, 70%, six steps; (e) $HOP(O)(OBu)_2$, 4 Å MS, 97%; (f) TIPSCl, $NEt_3$, DMAP, $CH_2Cl_2$, 91%; (g) AllOH, $BF_3\text{-}Et_2O$, $CH_2Cl_2$, 99%.

The previously reported synthetic route to the differentially protected myo-inositol by Fraser-Reid et al., J Chem Soc, Perkin Trans 1 1998:631 was modified (Scheme 4). Methyl glucopyranose was quantitatively converted to 15 in three consecutive steps. A Parikh-Doering reaction oxidized the primary hydroxyl group in 15 to an aldehyde in quantitative yield. Using this oxidation, complications arising from the urea byproduct created when dicyclohexylcarbodiimide Scheme 3. Efficient multi-gram preparations of mannose building blocks via bicyclic and tricyclic orthoester intermediates

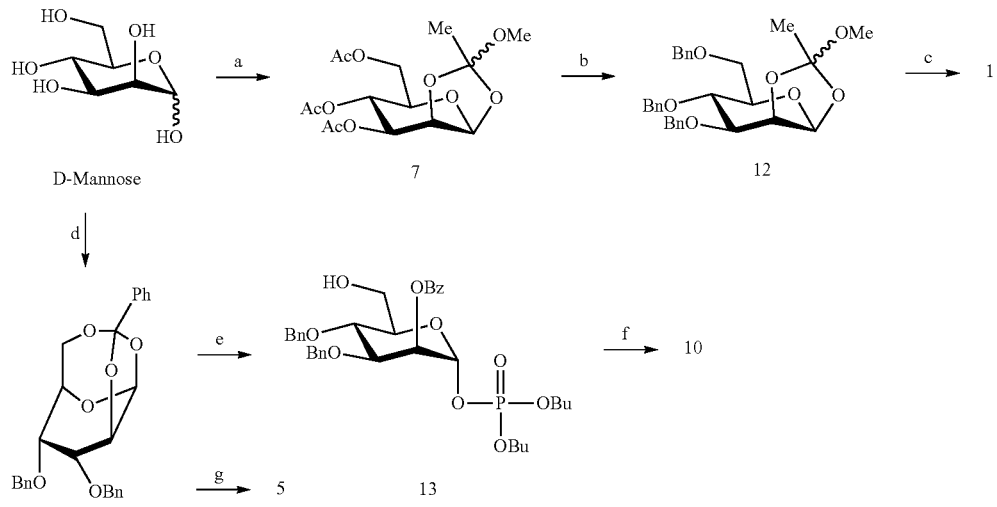

(DCC) was used as activator were avoided. The sulfate byproduct was readily removed by water extraction. The partially protected myo-inositol 16 was prepared from compound 15 in 40% yield over four consecutive steps. The allyl and NAP protecting groups were introduced at C1 and C2 of the D-myo-inositol respectively to furnish 11, ready for further decoration at the C6 hydroxyl group.

Scheme 4. Synthesis of 1-O-acetyl-3,4,5-tri-O-bynzyl-myo-inositol (16)

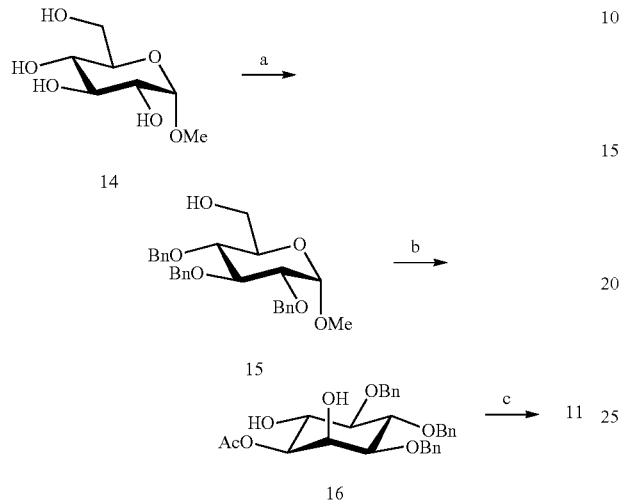

Reagents and conditions: (a) i. Imidazole, TIPSCl, DMF 0° C. to rt, ii. NaH, BnBr, DMF, 0° C. to rt, iii. TBAF, THF, 99%, three steps; (b) i. SO₃-Py, DIPEA, DMSO, CH₂Cl₂, 0° C. to rt, ii. K₂CO₃, Ac₂O, MeCN, reflux, iii. Hg(CF₃COO)₂, Acetone/H₂O (4:1), rt, 1 h, then NaOAc (aq), NaCl (aq), 0° C. to rt, iv. NaBH(CH₃COO)₃, AcOH, MeCN, 0° C. to rt, 40%, four steps. (c) (i) CH₂CHOEt, PPTS, then NaOMe, MeOH, (ii) AllBr, NaH, then 2N HCl, 84%, two steps, (III) NAPBr, NaH, TBAI, DMF, 81%;

Assembly of Myo-Inositol Containing Pseudosaccharides.

The myo-inositol containing pseudotrisaccharide 8 was assembled in a stepwise manner. Glycosylation of inositol 11 with mannosyl phosphate 10 that contained a C6-TIPS ether as temporary protecting group was found to be optimal at −40° C., in toluene, and promoted by a stoichiometric amount of TMSOTf (Scheme 5). Under these conditions the reaction gave a good yield with complete α-selectivity. To sustain further glycosylations, the temporary TIPS protecting group was replaced by the levulinoyl (Lev) group. The presence of TIPS rather than Lev on the C6 hydroxyl group of 10 was found necessary to balance its reactivity with inositol 10 to obtain high yield and selectivity. Treatment of 19 with DDQ unmasked the C2 hydroxyl group on inositol to give 20 that served in turn as nucleophile during the next mannosylation.

Scheme 5. Assembly of myo-inositol containing pseudotrisaccharide 8

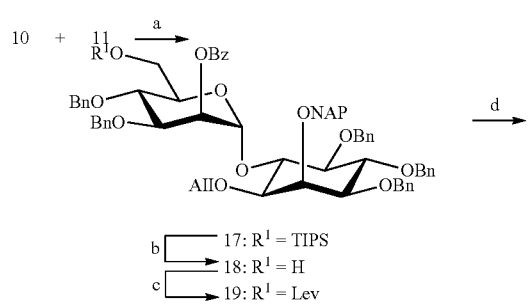

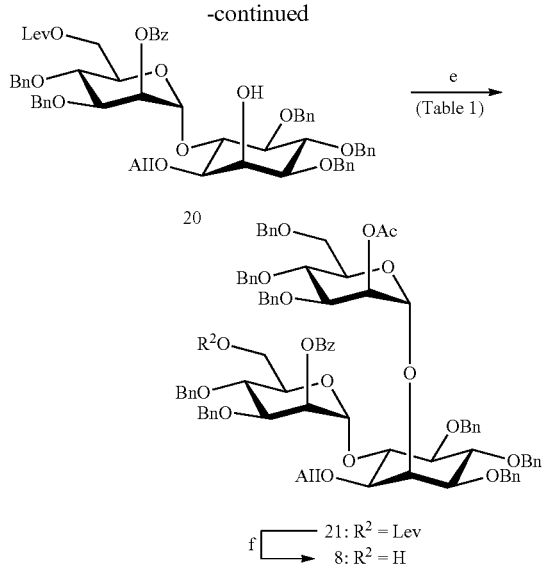

Reagents and conditions: (a) TMSOTf, Toluene, −40° C., 90%; (b) AcCl, MeOH, CH₂Cl₂, 0° C., quant.; (c) LevOH, DIPC, DMAP, quant.; (d) DDQ, CH₂Cl₂, MeOH, 0° C., 95%; (e) 1, TBDMSOTf, Toluene, −40° C., 95%, (see Table 1); (f) H₂NNH₃OAc, MeOH, rt, 89%.

TABLE 1

Effects of promoter and temperature on the glycosylation of glycosyl phosphate 1 and myo-inositol intermediate 20

| Entry | Promoter | Temperature (° C.) | Yield (%) |
|---|---|---|---|
| 1 | TMSOTf | −40 | 15 |
| 2 | TBDMSOTf | −40 | 27 |
| 3 | TBDMSOTf | −10 | 57 |
| 4 | TBDMSOTf | 0 | 55 |
| 5 | TBDMSOTf | rt | 95 |

The second mannosylation on the C2 hydroxyl group of pseudodisaccharide 20 was found to be nontrivial (Table 1). Activation by TMSOTf afforded the desired pseudodisaccharide 21 in just 15% yield (Table 1, Entry 1). Decomposition of 1 to form the anomeric alcohol was observed instead. Switching the promoter from TMSOTf to the milder activator TBDMSOTf dramatically improved the yield of the desired product (Table 1, Entry 2). This observation suggested a possible reactivity mismatch between highly activated 1 and less activated 20. The glycosylation was thus improved by reducing the reactivity of 1 with TBDMSOTf. Product 21 was obtained in excellent yield (95%) and selectivity by performing the glycosylation at 0° C. (Table 1, Entry 5). The α linkages in 21 were confirmed by 2D NMR. $^1$H-$^{13}$C coupled HSQC NMR indicated $^1$H1-$^{13}$C1 coupling constants ($J_{C1,H1}$) of 178 Hz at the anomeric position of the mannose connected to the C2 of inositol and 182 Hz at the anomeric position of the mannose on C6 of inositol. $J_{C1,H1}$ of β mannosidic linkages are typically lower at around 159 Hz (C. A. Podlasek et al., J Am Chem Soc 2006, 128:33638-3648).

Removal of the Lev group in 21 was achieved by treatment with hydrazine acetate in methanol and required careful monitoring. Longer reaction times resulted predominantly in the reduction of the allyl moiety to a propyl group. Partially protected inositol 16 was subjected to protecting group manipulations to furnish the inositol intermediates for PI and PIM₁ (Scheme 6). Based on reactivity differences, the equatorial C6 hydroxyl group of the diol 22 was selectively acetylated to afford 23 as the intermediate en route to PIM₁. The PI intermediate 24 was obtained in parallel by benzylation of the common intermediate 22.

Scheme 6. Protecting group manipulations on
myo-inositol 16 for PI intermediate 23 and PIM₁ intermediate 24

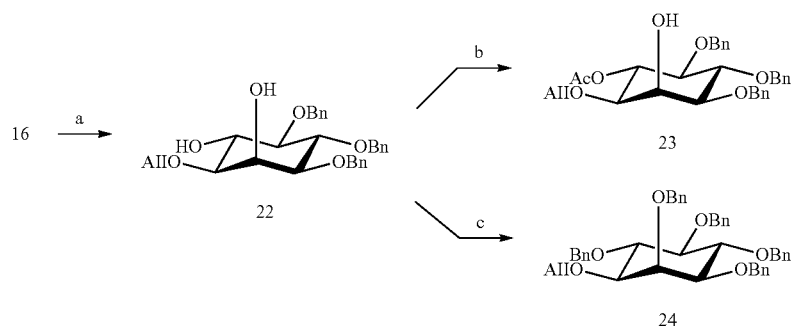

Reagents and conditions: (a) (i) CH₂CHOEt, PPTS, then NaOMe, MeOH, (ii) AllBr, NaH, then 2N HCl, 84%, two steps; (b) Ac₂O, DMAP, Py, 70%; (c) NaH, BnBr, DMF, 0° C. to rt, quant.

Assembly of oligomannoside fragments. The oligomannoside trichloroacetimidates 2, 3, and 4 were assembled in linear fashion (Scheme 7). All glycosylations employed mannosyl phosphate 1 and TMSOTf as activator. The α-1,6 glycosydic bond was readily formed at 0° C. in quantitative yield. A lower temperature (−40° C.) was required to efficiently install 1,2 glycosylic linkages with complete α-selectivity. Deallylation of 25-27 was performed by allylic substitutions mediated by a palladium complex to yield the corresponding anomeric alcohols 28-30. Finally, conversion to the glycosyl trichloroacetimidates 2-4 were carried out using sodium hydride as base.

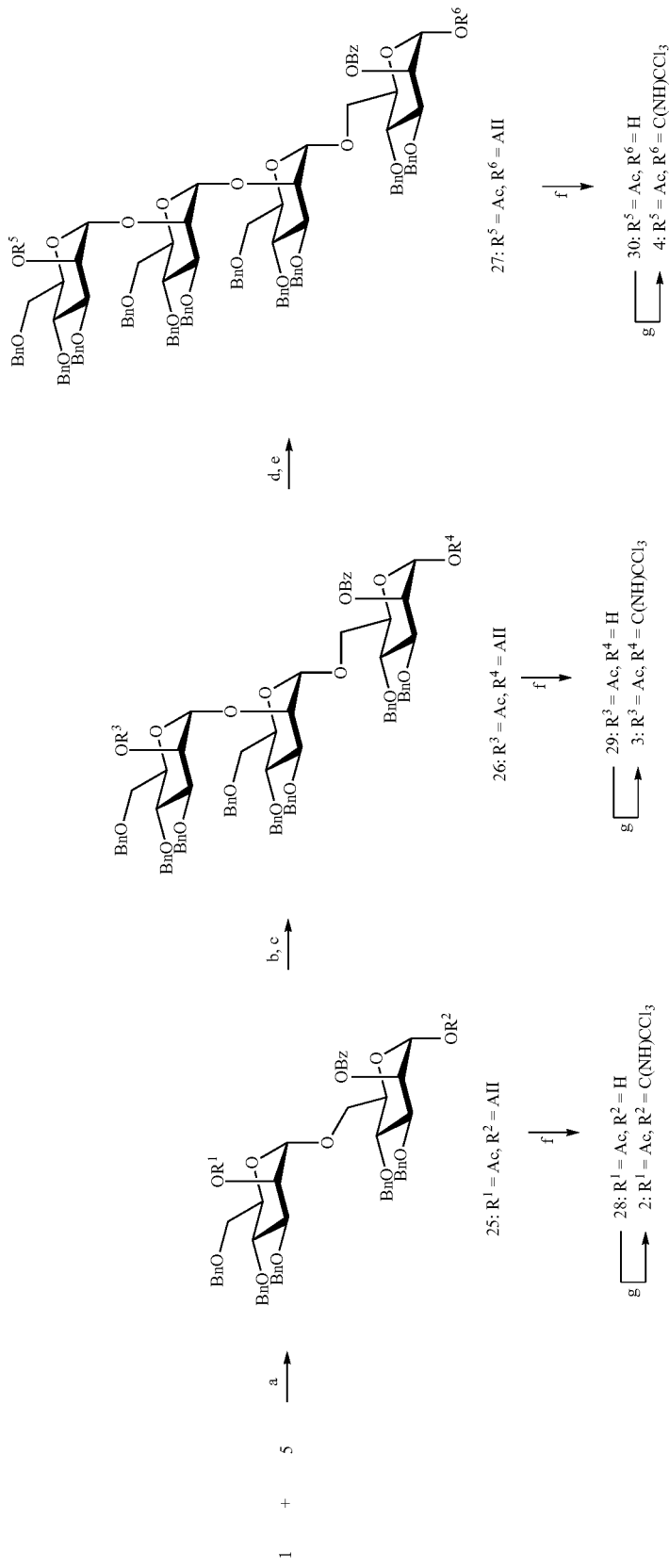
Scheme 7. Assembly of oligomannosylating reagents 2-4 for the synthesis of PIM$_2$-PIM$_8$ Reagents and conditions: (a) TMSOTf, $CH_2Cl_2$, $-10°$ C., quant.; (b) AcCl, MeOH, $CH_2Cl_2$, $0°$ C., 91%; (c) 1, TMSOTf, $-40°$ C., Toluene, 95%: (d) AcCl, MeOH, $CH_2Cl_2$, $0°$ C., 84%; (e) 1, TMSOTf, Toluene, $-40°$ C., 96%; (f) $Pd(OAc)_2$, MeOH, $PPh_3$, $Et_2NH$, 77% for 28, 95% for 29, and 83% for 30; (g) $Cl_3CCN$, NaH, rt, 85% for 2, 86% for 3, and 89% for 4.

Assembly of Protected PIM Backbones.

Prior to phosphorylation, all protected PIM oligosaccharide backbones were obtained by late-state glycosylations (Table 2). Following these glycosylations all ester protecting groups were removed with sodium methoxide in methanol at elevated temperature before masking the free hydroxyl groups as benzyl ethers. These protecting group manipulations were performed to avoid the persistence of O-benzoate protecting groups under Birch conditions in the final deprotection.

TABLE 2

Assembly of fully protected $PIM_1$-$PIM_6$ backbones: Union of (oligo)mannosyl fragment (X) and inositiol-containing pseudosaccharide fragment (Y)

$X + Y$ →
a) Glycosylation (except entry 2)
b) NaOMe/MeOH, $50°$ C., 24 h
c) BnBr, NaH, $0°$ C. to rt, 12 h
→ Differentially Protected $PIM_2$-$PIM_6$

| Entry | X | Y | Glycosylation conditions | Products |
|---|---|---|---|---|
| 1 | 1 | 23 | TMSOTf, $-40°$ C., $Et_2O$ | 31 |
| 2 | Not applied | 8 | No glycosylation | 32: $R^1 = Bn$ |
| 3 | 1 | 8 | TMSOTf, $-10°$ C., $CH_2Cl_2$ | 33: $R^1 =$ |
| 4 | 2 | 8 | TMSOTf, $-10°$ C., $CH_2Cl_2$ | 34: $R^1 =$ |

TABLE 2-continued

Assembly of fully protected PIM$_1$-PIM$_6$ backbones: Union of (oligo)mannosyl fragment (X) and inositiol-containing pseudosaccharide fragment (Y)

X + Y  a) Glycosylation (except entry 2)
b) NaOMe/MeOH, 50° C., 24 h
c) BnBr, NaH, 0° C. to rt, 12 h
→ Differentially Protected PIM$_2$-PIM$_6$

| Entry | X | Y | Glycosylation conditions | Products |
|---|---|---|---|---|
| 5 | 3 | 8 | TMSOTf, −10° C., CH$_2$Cl$_2$ | 35: R$^1$ = [structure] |
| 6 | 4 | 8 | TMSOTf, 0° C., CH$_2$Cl$_2$ | 36: R$^1$ = [structure] |

Coupling between mannosyl phosphate 1 and inositol 23 gave pseudodisaccharide 31, the backbone of PIM$_1$. To access the PIM$_2$ backbone, pseudotrisaccharide fragment 8 was directly used as the starting material to be transformed into backbone 32. The glycosylation products from couplings (Table 2, entry 3-5) between the oligomannosyl trichloroacetimidates (1-3) and the common pseudotrisaccharide 8 were cleanly achieved at −10° C. After quenching with triethylamine, the concentrated crude products were directly converted to obtain the benzylated products. When the larger structure 4 was used for glycosylation, the coupling became more sluggish and resulted in the hydrolysis of 4. A higher temperature (0° C.) was needed to obtain the 4+3 glycosylation product 46 (see experimental section). Pseudoheptasaccharide 46 was the largest oligosaccharide assembled in this series and consisted of fragments of all smaller oligosaccharides. Thus, 46 was analyzed extensively by C—H coupled HSQC to confirm its structural identity. 2D-NMR data elucidated six anomeric proton signals with typical α-manno $J_{C1,H1}$ couplings.

Removal of O-Allyl Protecting Group on Inositol.

Protocols to cleave the C-1 O-allyl group on inositol attached to oligosaccharides, performed by using PdCl$_2$, usually give moderate yields. Different methods to remove the O-allyl group were explored on substrate 31 (Scheme 8 and Table 3). The hydrogen activated iridium complex Ir {(COD)[PH$_3$(C$_6$H$_5$)$_2$]$_2$} PF$_6$ was found to be the most efficient reagent to isomerize the allyl group to the corresponding enol ether. In the same pot, a catalytic amount of p-toluenesulfonic acid (p-TsOH) was added to cleave the enol ether and liberate the C1 hydroxyl of pseudo-disaccharide 38 in quantitative yield. This two step procedure was applied to the larger oligosaccharides 32 to 36 as well. However, while the isomerizations mediated by the iridium complex worked smoothly, an excess of p-TsOH (10 equiv.) was required to cleave the enol ether and furnish 39-43 (Scheme 8, entry 3).

Scheme 8. Removal of allyl protecting groups on C1 myo-inositol of fully protected PI and PIM$_2$-PIM$_6$

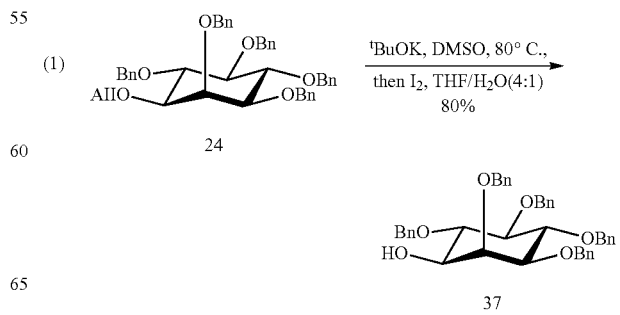

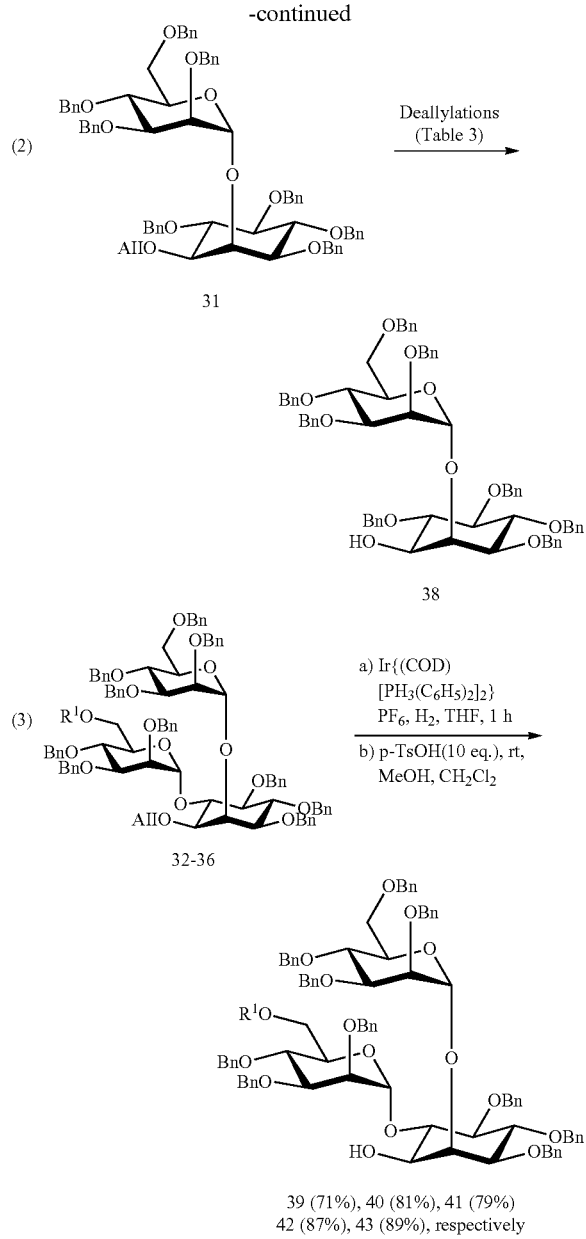

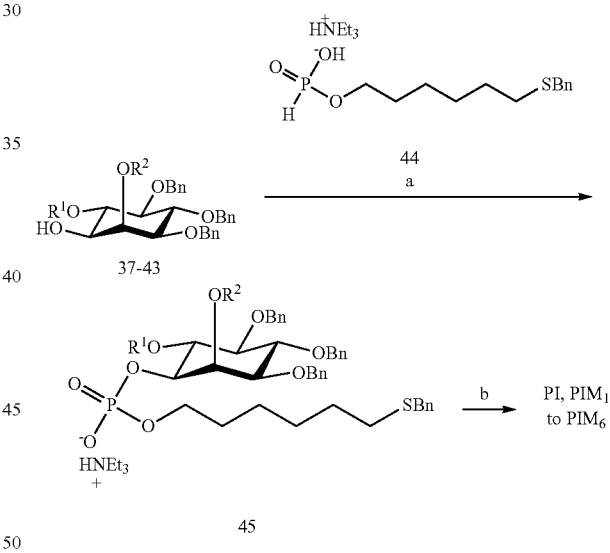

(Scheme 9). Substrates 37-43 were treated with pivaloyl chloride in the presence of linker 44 and pyridine. Subsequently, in the same pot, the H-phosphonate diesters were oxidized with iodine and water to provide the fully benzylated phosphodiesters 45 as triethylamine salts in excellent yield. Global removal of benzyl protecting groups of analogs 45(a-g) was achieved under Birch reduction conditions. The fully protected compounds were treated with sodium dissolved in ammonia to furnish the final products PI and $PIM_1$-$PIM_6$ with a sulfhydrylhexyl residue $R^2$. Small amounts of incompletely reduced products were observed containing some remaining benzyl groups. These side products were separated by extraction with chloroform and converted to the final products by re-submission to Birch reduction. The final products were formed as a mixture of monomers and disulfide dimers. Treatment with one equivalent of tris(carboxyethyl) phosphine hydrochloride (TCEP) immediately prior to conjugation of the final compounds ensured that PI and $PIM_1$-$PIM_6$ with a sulfhydrylhexyl residue $R^2$ were present as monomers.

The procedure may easily adapted in using a linker 44 with different length of alkyl chain and/or with a different protected functional group, e.g. carrying a maleimido functional group, a protected amino function or a protected carboxylic acid function.

Scheme 9. Phosphorylation of oligasoccharides 37-43 and global deprotection under Birch reduction conditions

TABLE 3

Removal of allyl protecting group on pseudo-disaccharide 31

| Entry | Conditions | Yield |
|---|---|---|
| 1 | $^t$BuOK, DMSO, 80° C., then $I_2$, THF/$H_2$O TMSOTf | 10%, (decomposition) |
| 2 | Pd(OAc)$_2$, PPh$_3$, HNEt$_2$, CH$_2$Cl$_2$/MeOH (2:1) | no reaction |
| 3 | [Ir(COD)(PCH$_3$Ph$_2$)$_2$]PF$_6$ (cat.), H$_2$, THF then $I_2$ in THF/$H_2$O (2:1) | 30% |
| 4 | [Ir(COD)(PCH$_3$Ph$_2$)$_2$]PF$_6$ (cat.), H$_2$, THF then p-TsOH (cat.) in DCM/MeOH (1:3) | quantitative |

Phosphorylation and Global Deprotection.

The phosphate moiety accompanied with a terminal thiol linker was installed on the inositol C1 hydroxyl group of the oligosaccharide backbone 37-43 using a H-phosphonate Reagents and conditions: (a) i. 44, PivCl, pyridine, ii. $I_2$, $H_2O$, pyridine, 90% to quant., 2 steps; b) i. Na/$NH_3$(I)/t-BuOH, −78° C., ii. MeOH, 65% for PI, 43% for $PIM_1$, 56% for $PIM_2$, 91% for $PIM_3$, 65% for $PIM_4$, 88% for $PIM_5$, and 84% for $PIM_6$.

PIM Microarrays to Determine Binding to DC-SIGN.

To study the interactions of synthetic PI and PIMs with the protein DC-SIGN on a microarray, PI and PIMs were immobilized on a maleimide activated glass slide via their thiol handle following established protocols. DC-SIGN is an important receptor on dendritic cells and contributes to the initiation of a pro-inflammatory response by host cells. One of the functions of DC-SIGN is the recognition of evolutionary conserved pathogenic structures that are secreted or exposed on the surface of viruses or bacteria. Upon binding to DC-SIGN, the antigens are internalized, processed and later presented on the surface of dendritic cells together with costimulatory molecules. *Mycobacteria* also use DC-SIGN as a receptor to enter dendritic cells (G. De Libero and L. Mori, Nat Rev Immunol 2005, 5:485-496).

Glass slides printed with the immobilized PI and $PIM_1$-$PIM_6$ were incubated with a DC-SIGN solution in buffer at room temperature to allow DC-SIGN to bind to the immobilized PIMs. Excess DC-SIGN was washed off and bound DC-SIGN was detected by incubation with a fluorescein-conjugated anti-DC-SIGN antibody. The difference in DC-SIGN binding affinity to the synthetic PIM compounds was assessed semi-quantitatively by monitoring the fluorescence intensity via a fluorescence scanner. Synthetic PIMs bind to DC-SIGN in a specific manner. Although both synthetic analogs of the most abundant $PIM_2$ and $PIM_6$ are recognized by DC-SIGN, the larger synthetic oligosaccharides $PIM_5$ and $PIM_6$ bound to DC-SIGN to a greater extent. This observation underlines the significance of the α-1,2-mannose motif present in both PIMs and ManLAM structures.

Adjuvant Activity of PIMs.

Figure 4:
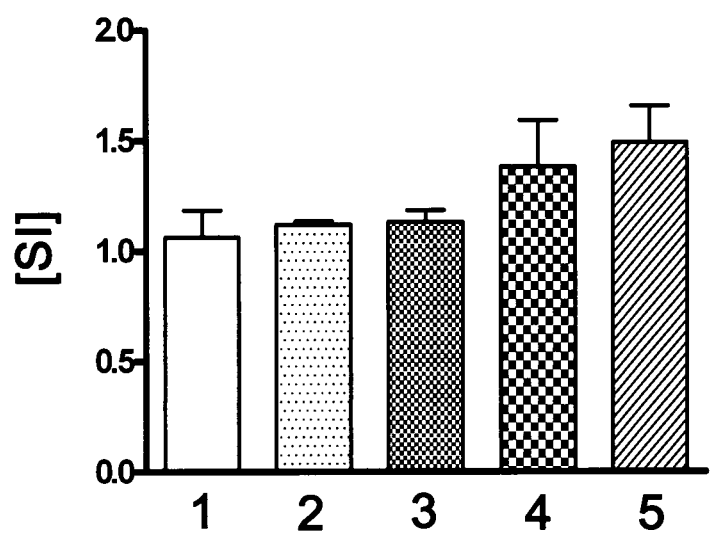
Figure 5:
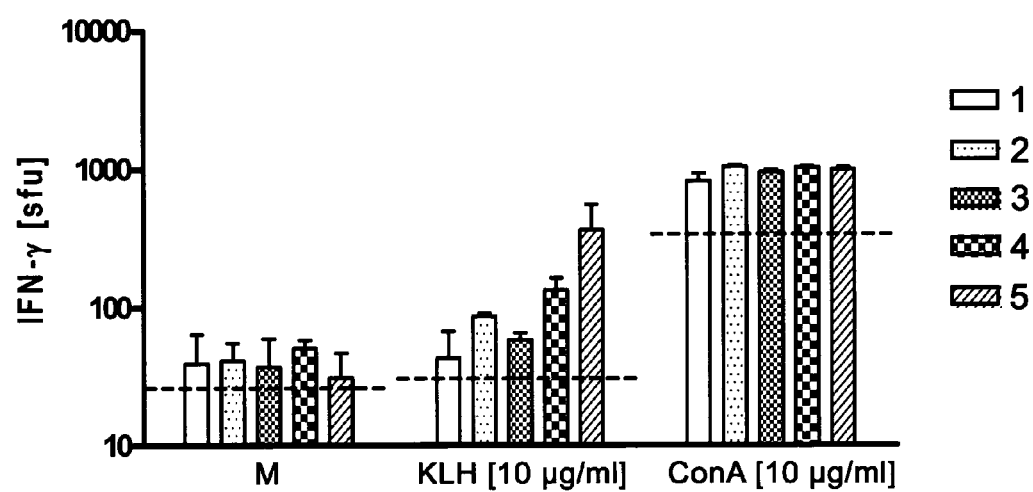

An important feature of natural PIMs is their ability to induce a host cell immune response. To investigate immunostimulatory effects of these synthetic PIMs four C57BL/6 mice per group were prime-boost immunized with the model antigen keyhole-limpet hemocyanin (KLH) covalently linked to $PIM_2$ and $PIM_6$. As expected, immunization with the pure antigen KLH resulted in detectable anti-KLH antibody levels. Antibody production in the presence of the well-established adjuvants Freund's adjuvant, alum and CpG, increased substantially. In comparison, conjugation of $PIM_6$ glycan to KLH also resulted in a marked increase of anti-KLH antibodies that was statistically significant for each serum dilution compared to KLH alone (FIG. 2). To address the mechanism by which the increased antibody production after covalent attachment of $PIM_6$ to KLH was caused, spleen cells of immunized mice were restimulated with KLH ex vivo and proliferation measured. Spleen cell proliferation of mice that had been immunized with KLH-$PIM_6$ was significantly increased indicating that T cell priming was stimulated by $PIM_6$ glycan (FIG. 4). It is also known that adjuvant properties not only depend on antibody production and T cell proliferation, but also on other T effector functions such as cytokine production. To this end, IFN-γ production of T cells was measured by ELISpot analysis. The frequency of IFN-γ producing T cells in spleen was determined upon restimulation of T cells with KLH. The ability of T cells to produce IFN-γ was increased in spleen cells of mice that had been immunized with KLH-$PIM_6$ conjugate (FIG. 5). The effect was even stronger than with the well-established adjuvants Freund's adjuvant, alum or CpG (CpG oligonucleotide ODN 1585, murine TLR9 ligand), which highlights the immunostimulatory capacity of synthetic $PIM_6$ glycan. Concanavalin A was used as a positive control since it serves as a T cell mitogen and stimulates all T cells to the same extent.

Recognition of $PIM_6$ by pattern recognition receptors on antigen-presenting cells might provide a danger signal, thereby facilitating enhanced uptake of the model antigen and increased expression of costimulatory molecules. The effect of $PIM_6$ on T cell proliferation and T cell effector functions such as IFN-γ production clearly indicates that antigen presentation by APCs and T cell activation are increased by $PIM_6$ glycan.

The synthetic PI and $PIM_6$-$PIM_6$ are suitable for conjugation with other appropriate surfaces such as fluorescent nanocrystals, beads or fluorophores to generate probes for cellular assays. Such tools may shed light on the mechanism by which PIM structures on Mtb can influence bacterial trafficking in host cells. The synthetic compounds can also be attached to affinity columns in search for proteins or enzymes in cell lysates that interact with PIMs. Moreover, the synthetic PIMs can be used as substrates to explore biosynthetic pathways of the PIMs.

Synthetic PIMs are useful as antigens to elicit an immune response against Mtb as well as adjuvants in vivo. For these purposes, the synthetic compounds are conjugated to different antigens.

EXAMPLES

General Procedures for Glycosylations

Glycosylating agent and nucleophile were co-evaporated with anhydrous toluene (3×) in vacuo and placed under high vacuum for at least 4 h. Glycosylations were performed without molecular sieves. Under argon atmosphere, the glycosylating agent and nucleophile mixtures were dissolved in a solvent at room temperature (rt) before being cooled to a desired temperature (0° C. by ice-water bath, −10° C. by ice-acetone bath, and −40° C. by dry ice-acetonitrile bath). A promoter (TMSOTf or TBDMSOTf) was added to this reaction solution in one portion via syringe. After the reaction had finished, excess triethylamine ($NEt_3$) was added to quench the reaction at the reaction temperature. The reaction mixture was concentrated in vacuo and purified by flash silica column chromatography or directly used as a starting material in the next reaction.

(2-O-Benzoyl-3,4-di-O-benzyl-6-O-triisopropylsilyl-α-D-mannopyranosyl)-(1→6)-1-O-allyl-2-O-napthyl-methyl-3,4,5-tri-O-benzyl-D-myo-inositol (17)

Following the general procedures for glycosylations, a glycosylation of mannosyl phosphate 10 (122 mg, 0.150 mmol) and inositol 11 (86 mg, 0.136 mmol) promoted by TMSOTf (29 μL, 0.150 mmol) was carried out in toluene (4 mL) at −40° C. for 2 h. After being quenched by $NEt_3$ (60 μL), the reaction mixture was concentrated in vacuo and purified by flash silica column chromatography (cyclohexane/EtOAc) to obtain the title compound 17 in quantitative yield as a white solid. $R_f$ 0.51 (cyclohexane/EtOAc=4:1); $[\alpha]_D^{r.t.}=-6.8$ (c=1.0, $CHCl_3$); b.p.=130.5-132° C.; $^1$H NMR (300 MHz, $CDCl_3$) δ 8.24-8.15 (m, 2H), 7.92-7.78 (m, 4H), 7.68-7.58 (m, 2H), 7.55-7.44 (m, 4H), 7.44-7.13 (m, 25H), 6.12-5.91 (m, 1H), 5.79 (dd, J=1.9, 3.0, 1H), 5.58 (d, J=1.5, 1H), 5.37-5.15 (m, 2H), 5.10-4.60 (m, 12H), 4.40-3.89 (m, 8H), 3.61 (brs, 2H), 3.52-3.24 (m, 3H), 1.20-1.03 (m, 21H); HRMS-MALDI (m/z): $[M+Na]^+$ calculated for $C_{77}H_{88}O_{12}SiNa$, 1255.5937; Found: 1255.5911.

(2-O-Benzoyl-3,4-di-O-benzyl-6-O-levuniloyl-α-D-mannopyranosyl)-(1→6)-1-O-allyl-2-O-(2-O-acetyl-3,4,6-tri-O-benzyl-α-D-mannopyranosyl)-3,4,5-tri-O-benzyl-D-myo-inositol (21)

Following the general procedures for glycosylations, a glycosylation of mannosyl phosphate 1 (225 mg, 0.217 mmol) and pseudodisaccharide 20 (238 mg, 0.347 mmol) promoted by TBDMSOTf (85 μL, 0.370 mmol) was carried out in toluene (5 mL) at 0° C. for 1 h. After being quenched by $NEt_3$ (100 μL), the reaction mixture was concentrated in vacuo and purified by flash silica column chromatography (cyclohexane/EtOAc gradient) to obtain the title compound 21 (311.1 mg, 95%) as a colorless syrup. $R_f$ 0.33 (cyclohexane/EtOAc=7:3); $[\alpha]_D^{r.t.}=+9.3$ (c=1.0, $CHCl_3$); $^1$H NMR (600

MHz, CDCl₃) δ 8.11-8.05 (m, 2H), 7.60-7.54 (m, 1H), 7.49-7.42 (m, 2H), 7.38-7.09 (m, 40H), 5.96-5.85 (m, 1H), 5.65 (dd, J=2.1, 2.9, 1H), 5.53 (d, J=1.8, 1H), 5.42 (dd, J=2.0, 2.9, 1H), 5.23-5.17 (m, 1H), 5.12 (d, J=1.8, 1H), 5.11-5.09 (m, 1H), 5.00-4.68 (m, 8H), 4.65-4.25 (m, 9H), 4.20-3.78 (m, 12H), 3.51 (dd, J=3.5, 10.8, 1 H), 3.36-3.23 (m, 4H), 2.74-2.42 (m, 4H), 2.08 (s, 3H), 2.07 (s, 3H); HRMS-MALDI (m/z): [M+Na]⁺ calculated for $C_{91}H_{96}O_{20}Na$, 1531.6387; Found: 1531.6372.

(2-O-Benzoyl-3,4-di-O-benzyl-α-D-mannopyranosyl)-(1→6)-1-O-allyl-2-O-(2-O-acetyl-3,4,6-tri-O-benzyl-α-D-mannopyranosyl)-3,4,5-tri-O-benzyl-D-myo-inositol (8)

A solution of trisaccharide 21 (840 mg, 0.556 mmol) and hydrazine acetate (256 mg, 2.782 mmol) in a mixture of CH₂Cl₂ (30 mL) and MeOH (15 mL) was stirred at rt. After 4 h, although there was a small amount of the starting material 21 left, the reaction was quenched by adding pyridine (15 mL) and acetone (15 mL) in order to avoid the reduction of the allyl group on the desired product by hydrazine acetate. The reaction mixture was concentrated in vacuo and purified by flash silica column chromatography (cyclohexane/EtOAc) to obtain the title compound 8 (698.9 mg, 89%) as a colorless syrup. $R_f$ 0.40 (cyclohexane/EtOAc=7:3); $[α]_D^{r.t.}$=+14.1 (c=1.0, CHCl₃); ¹H NMR (600 MHz, CDCl₃) δ 8.08-8.03 (m, 2H), 7.59-7.53 (m, 1H), 7.48-7.41 (m, 2H), 7.38-7.08 (m, 40H), 5.95-5.83 (m, 1H), 5.65 (dd, J=1.9, 3.1, 1H), 5.54 (d, J=1.8, 1H), 5.46 (dd, J=1.9, 3.0, 1H), 5.22-5.18 (m, 1H), 5.17 (d, J=1.7, 1H), 5.09 (dd, J=1.4, 10.4, 1H), 4.97-4.51 (m, 14H), 4.43-4.26 (m, 3H), 4.18-3.76 (m, 10H), 3.55-3.23 (m, 7H), 2.08 (s, 3H), 1.86 (brs, 1H); HRMS-MALDI (m/z): [M+Na]⁺ calculated for $C_{86}H_{90}O_{18}Na$, 1433.6019; Found: 1433.5996.

1-O-Allyl-2-O-(2,3,4,6-tetra-O-benzyl-α-D-mannopyranosyl)-3,4,5,6-tetra-O-benzyl-D-myo-inositol (31)

Following the general procedures for glycosylations, a glycosylation of mannosyl phosphate 1 (273.8 mg, 0.400 mmol) and inositol 23 (194.0 mg, 0.364 mmol) promoted by TMSOTf (76 μL, 0.400 mmol) was carried out in Et₂O (8 mL) at −40° C. for 1.5 h. After being quenched by NEt₃ (150 μL), the reaction mixture was concentrated in vacuo and purified by flash silica column chromatography (cyclohexane/EtOAc) to obtain 1-O-allyl-2-O-(2-O-acetyl-3,4,6-tri-O-benzyl-α-D-mannopyranosyl)-3,4,5-tri-O-benzyl-6-O-acetyl-D-myo-inositol 31p (266.0 mg, 70%) as a colorless syrup. $[α]_D^{r.t.}$=+14.5 (c=1.0, CHCl₃); ¹H NMR (300 MHz, CDCl₃) δ 7.49-7.07 (m, 30H), 5.93-5.70 (m, 1H), 5.57 (dd, J=2.1, 2.7, 1 H), 5.46 (t, J=10.0, 1H), 5.28-5.21 (m, 2H), 5.21-5.11 (m, 2H), 4.93-4.70 (m, 6H), 4.68-4.53 (m, 4H), 4.47-4.23 (m, 3H), 4.21-4.04 (m, 2H), 4.03-3.84 (m, 4H), 3.59-3.18 (m, 5H), 2.17-2.10 (m, 3H), 1.97 (s, 3H); HRMS-MALDI (m/z): [M+Na]⁺ calculated for $C_{61}H_{66}O_{13}Na$, 1029.4396; Found: 1029.4400. To a solution of pseudodisaccharide 31p (266 mg, 0.288 mmol) in a mixture of CH₂Cl₂ (1 mL) and MeOH (3 mL), a solution of NaOMe in MeOH (1.150 μL of 0.288 M, 0.180 mmol, freshly prepared from Na(s) and MeOH) was added at rt. The reaction was stirred at rt for 2 d, concentrated in vacuo, and filtered through a short plug of silica gel to obtain a yellow syrup. A solution of this crude product and BnBr (121 μL, 1.018 mmol) in DMF (8 mL) was cooled to 0° C. and NaH (60% in mineral oil, 40.7 mg, 1.018 mmol) was added. The reaction mixture was allowed to warm to rt. After 5 h at rt, the reaction was quenched by carefully adding MeOH (1 mL) dropwise. The reaction mixture was diluted with EtOAc (20 mL), washed with water (2×) and brine, dried over MgSO₄, and concentrated in vacuo. The crude product was purified by flash silica column chromatography (cyclohexane/EtOAc) to obtain the title compound 31 in quantitative yield (2 steps) as a colorless syrup. NMR spectra are the same as reported in literature (C. J. J. Elie et al., Tetrahedron 1989, 45:3477-3486).

(2,3,4,6-Tetra-O-benzyl-α-D-mannopyranosyl)-(1→6)-1-O-allyl-2-O-(2,3,4,6-tetra-O-benzyl-α-D-mannopyranosyl)-3,4,5-tri-O-benzyl-D-myo-inositol (32)

To a solution of pseudotrisaccharide 8 (59.7 mg, 0.042 mmol) in a mixture of THF (1 mL) and MeOH (1 mL) a solution of NaOMe in MeOH (168 μL of 0.250 M, 0.042 mmol, freshly prepared from Na(s) and MeOH) was added at rt. The reaction was stirred at rt for 3 d and neutralized with acid resin (methanol washed Amberlite IR-120). The resin was filtered off and the reaction solution was concentrated in vacuo and placed under high vacuum for 4 h. A solution of this crude product and BnBr (20 μL, 0.168 mmol) in DMF (4 mL) was cooled to 0° C. and NaH (60% in mineral oil, 7 mg, 0.168 mmol) was added. The reaction mixture was allowed to warm to rt. After 12 h at rt, the reaction mixture was transferred to a separatory funnel and carefully quenched by minimum amount of MeOH and water (10 mL). The reaction mixture was extracted with EtOAc (3×10 mL). The combined organic layer was washed with brine, dried over Na₂SO₄, and concentrated in vacuo. The crude product was purified by flash silica column chromatography (cyclohexane/EtOAc) to obtain the title compound 32 (58 mg, 90%, 2 steps) as a colorless syrup. $R_f$ 0.27 (hexanes/EtOAc=3:1); $[α]_D^{r.t.}$=+26.4 (c=1.8, CHCl₃); ¹H NMR (500 MHz, CDCl₃) δ 7.41-6.96 (m, 55H), 5.70 (ddd, J=5.5, 10.6, 22.7, 1 H), 5.48 (d, J=1.7, 1 H), 5.22 (d, J=1.4, 1H), 5.21-5.16 (m, 1H), 5.08-5.04 (m, 1H), 4.93-4.25 (m, 22H), 4.20-3.72 (m, 13H), 3.49 (dd, J=3.7, 10.7, 1 H), 3.42-3.07 (m, 6H); HRMS-MALDI (m/z): [M+Na]⁺ calculated for $C_{98}H_{102}O_{16}Na$, 1557.7030; Found: 1557.7030.

(2,3,4,6-Tetra-O-benzyl-α-D-mannopyranosyl)-(1→6)-(2,3,4-tri-O-benzyl-α-D-manno-pyranosyl)-(1→6)-1-O-allyl-2-O-(2,3,4,6-tetra-O-benzyl-α-D-mannopyranosyl)-3,4,5-tri-O-benzyl-D-myo-inositol (33)

Following the general procedures for glycosylations, a glycosylation of mannosyl phosphate 1 (54.0 mg, 0.079 mmol) and pseudotrisaccharide 8 (70.0 mg, 0.049 mmol) promoted by TMSOTf (12 μL, 0.064 mmol) was carried out in CH₂Cl₂ (3 mL) at −10° C. for 1 h. After being quenched by NEt₃ (40 μL), the reaction mixture was concentrated in vacuo. To a solution of this crude product in THF (2 mL), a solution of NaOMe in MeOH (2.00 mL of 0.250 M, 0.500 mmol, freshly prepared from Na(s) and MeOH) was added at rt. The reaction was stirred at 50° C. for 12 h and neutralized with acid resin (methanol washed Amberlite IR-120). The reaction mixture was filtered through a short plug of silica gel, concentrated in vacuo and placed under high vacuum for 4 h. A solution of this crude product and BnBr (59 μL, 0.496 mmol) in DMF (4 mL) was cooled to 0° C. and NaH (60% in mineral oil, 20 mg, 0.496 mmol) was added. The reaction mixture was allowed to warm to rt. After 12 h at rt, the reaction mixture was transferred to a separatory funnel and carefully quenched by minimum amount of MeOH and water (10 mL). The reaction mixture was extracted with EtOAc (3×10 mL). The combined organic layer was washed with brine, dried over $Na_2SO_4$, and concentrated in vacuo. The crude product was purified by general procedures for glycosylations flash silica column chromatography (cyclohexane/EtOAc) to obtain the title compound 33 (86.5 mg, 89%, 3 steps) as a colorless syrup. $R_f$ 0.27 (cyclohexane/EtOAc=4:1); $[\alpha]_D^{r.t.}$=+35.6 (c=1.0, $CHCl_3$); $^1$H NMR (300 MHz, $CDCl_3$) δ 7.50-7.09 (m, 70H), 5.77 (ddd, J=5.4, 10.6, 22.5, 1H), 5.50 (d, J=1.1, 1H), 5.29 (brs, 1.5H), 5.23 (d, J=1.3, 0.5H), 5.15 (d, J=0.9, 0.5H), 5.11 (brs, 1.5H), 5.08-4.76 (m, 7H), 4.76-4.26 (m, 22H), 4.26-3.80 (m, 15H), 3.62-3.13 (m, 10H); ESI-MS (m/z): $[M+NH_4]^{1+}$ calculated for $C_{125}H_{134}NO_{21}$, 1984.9; Found: 1984.4 as a dominant peak.

(2,3,4,6-Tetra-O-benzyl-α-D-mannopyranosyl)-
(1→6)-(2,3,4-tri-O-benzyl-α-D-manno-Pyranosyl)-
(1→6)-(2,3,4-tri-O-benzyl-α-D-mannopyranosyl)-
(1→6)-1-O-allyl-2-O-(2,3,4,6-tetra-O-benzyl-α-D-mannopyranosyl)-3,4,5-tri-O-benzyl-D-myo-inositol (34)

Following the general procedures for glycosylations, a glycosylation of mannosyl imidate 2 (102.0 mg, 0.094 mmol) and pseudotrisaccharide 8 (110.0 mg, 0.078 mmol) promoted by TMSOTf (1.8 μL, 0.008 mmol) was carried out in $CH_2Cl_2$ (3 mL) at −10° C. for 1 h. After being quenched by $NEt_3$ (10 μL), the reaction mixture was concentrated in vacuo. To a solution of this crude product in THF (2 mL), a solution of NaOMe in MeOH (3.1 mL of 0.250 M, 0.780 mmol, freshly prepared from Na(s) and MeOH) was added at rt. The reaction was stirred at 60° C. for 18 h and neutralized with acid resin (methanol washed Amberlite IR-120). The reaction mixture was filtered through a short plug of silica gel, concentrated in vacuo and placed under high vacuum for 4 h. A solution of this crude product and BnBr (52 μL, 0.441 mmol) in DMF (4 mL) was cooled to 0° C. and NaH (60% in mineral oil, 23.5 mg, 0.588 mmol) was added. The reaction mixture was allowed to warm to rt. After 12 h at rt, the reaction mixture was transferred to a separatory funnel and carefully quenched by minimum amount of MeOH and water (10 mL). The reaction mixture was extracted with EtOAc (3×10 mL). The combined organic layer was washed with brine, dried over $Na_2SO_4$, and concentrated in vacuo. The crude product was purified by flash silica column chromatography (cyclohexane/EtOAc) to obtain the title compound 34 (166.4 mg, 89%, 3 steps) as a colorless syrup. $R_f$ 0.30 (cyclohexane/EtOAc=7:3); $[\alpha]_D^{r.t.}$=+38.7 (c=1.0, $CHCl_3$); $^1$H NMR (500 MHz, $CDCl_3$) δ 7.47-7.05 (m, 85H), 5.82-5.68 (m, 1H), 5.45 (brs, 1H), 5.24 (brs, 1.5H), 5.21 (brs, 0.5H), 5.12 (brs, 0.5H), 5.09 (brs, 1.5H), 5.07-4.76 (m, 9H), 4.75-4.30 (m, 27H), 4.22-3.79 (m, 18H), 3.69-3.48 (m, 5H), 3.46-3.09 (m, 8H); HRMS-MALDI (m/z): $[M+Na]^+$ calculated for $C_{152}H_{158}O_{26}Na$, 2422.0934; Found: 2422.0995.

(2,3,4,6-Tetra-O-benzyl-α-D-mannopyranosyl)-
(1→2)-(3,4,6-tri-O-benzyl-α-D-manno-pyranosyl)-
(1→6)-(2,3,4-tri-O-benzyl-D-mannopyranosyl)-
(1→6)-(2,3,4-tri-O-benzyl-α-D-mannopyranosyl)-
(1→6)-1-O-allyl-2-O-(2,3,4,6-tetra-O-benzyl-α-D-mannopyranosyl)-3,4,5-tri-O-benzyl-D-myo-inositol) (35)

Following the general procedures for glycosylations, a glycosylation of mannosyl imidate 3 (128.0 mg, 0.085 mmol) and pseudotrisaccharide 8 (100.0 mg, 0.071 mmol) promoted by TMSOTf (1.6 μL, 0.007 mmol) was carried out in $CH_2Cl_2$ (4 mL) at −10° C. for 1 h. After being quenched by $NEt_3$ (10 μL), the reaction mixture was concentrated in vacuo. To a solution of this crude product in THF (2 mL), a solution of NaOMe in MeOH (2.8 mL of 0.250 M, 0.710 mmol, freshly prepared from Na(s) and MeOH) was added at rt. The reaction was stirred at 60° C. for 12 h and neutralized with acid resin (methanol washed Amberlite IR-120). The reaction mixture was filtered through a short plug of silica gel, concentrated in vacuo and placed under high vacuum for 4 h. A solution of this crude product and BnBr (84 μL, 0.709 mmol) in DMF (4 mL) was cooled to 0° C. and NaH (60% in mineral oil, 28.3 mg, 0.709 mmol) was added. The reaction mixture was allowed to warm to rt. After 16 h at rt, the reaction mixture was transferred to a separatory funnel and carefully quenched by minimum amount of MeOH and water (10 mL). The reaction mixture was extracted with EtOAc (3×10 mL). The combined organic layer was washed with brine, dried over $Na_2SO_4$, and concentrated in vacuo. The crude product was purified by flash silica column chromatography (cyclohexane/EtOAc) to obtain the title compound 35 (145.0 mg, 73%, 3 steps) as a colorless syrup. $R_f$ 0.56 (cyclohexane/EtOAc=7:3); $[\alpha]_D^{r.t.}$=+38.5 (c=1.0, $CHCl_3$); $^1$H NMR (500 MHz, $CDCl_3$) δ 7.50-7.06 (m, 100H), 5.77 (ddd, J=5.5, 10.6, 22.6, 1H), 5.49 (d, J=1.4, 1H), 5.29-5.25 (m, 1.5H), 5.25-5.21 (m, 1.5H), 5.15-5.10 (m, 1H), 5.08-4.87 (m, 8H), 4.86-4.77 (m, 3H), 4.76-4.33 (m, 32H), 4.25-4.03 (m, 6H), 4.03-3.82 (m, 16H), 3.82-3.53 (m, 4H), 3.53-3.11 (m, 11H); HRMS-MALDI (m/z): $[M+Na]^+$ calculated for $C_{179}H_{186}O_{31}Na$, 2854.2870; Found: 2854.2804.

(2,3,4,6-Tetra-O-benzyl-α-D-mannopyranosyl)-
(1→2)-(3,4,6-tri-O-benzyl-α-D-manno-pyranosyl)-
(1→2)-(3,4,6-tri-O-benzyl-α-D-mannopyranosyl)-
(1→6)-(2,3,4-tri-O-benzyl-α-D-mannopyranosyl)-
(1→6)-(2,3,4-tri-O-benzyl-α-D-mannopyranosyl)-
(1→6)-1-O-allyl-2-O-(2,3,4,6-tetra-O-benzyl-α-D-mannopyranosyl)-3,4,5-tri-O-benzyl-D-myo-inositol) (36)

Following the general procedures for glycosylations, a glycosylation of mannosyl imidate 4 (164.0 mg, 0.084 mmol) and pseudotrisaccharide 8 (99.0 mg, 0.070 mmol) promoted by TMSOTf (1.6 μL, 0.007 mmol) was carried out in $CH_2Cl_2$ (6 mL) at 0° C. for 1 h. After being quenched by $NEt_3$ (10 μL), the reaction mixture was concentrated in vacuo and purified by recycling size exclusion HPLC (eluent=100% $CHCl_3$) to obtain (2-O-acetyl-3,4,6-tri-O-benzyl-α-D-mannopyranosyl)-(1→2)-(3,4,6-tri-O-benzyl-α-D-mannopyranosyl)-(1→2)-(3,4,6-tri-O-benzyl-α-D-mannopyranosyl)-(1→6)-(2-O-benzoyl-3,4-di-O-benzyl-α-D-mannopyranosyl)-(16)-(2-O-benzoyl-3,4-di-O-benzyl-α-D-mannopyranosyl)-(1→6)-1-O-allyl-2-O-(2-O-acetyl-3,4,6-tri-O-benzyl-α-D-mannopyranosyl)-3,4,5-tri-O-benzyl-D-myo-inositol) 36p (143.0 mg, 64%) as a colorless syrup. The remaining pseudotrisaccharide starting material 8 was also recovered (27.5 mg, 28%) as a colorless syrup. $R_f$ 0.44 (cyclohexane/EtOAc=7:3); $[\alpha]_D^{r.t.}$=+25.9 (c=1.0, $CHCl_3$); $^1$H NMR (600 MHz, $CDCl_3$) δ 8.17-8.01 (m, 4H), 7.50-6.87 (m, 101H), 5.90 (ddd, J=5.7, 10.5, 22.8, 1 H), 5.76 (dd, J=2.0, 2.9, 1H), 5.74 (dd, J=2.1, 2.9, 1H), 5.56 (dd, J=1.9, 3.2, 1H), 5.54 (d, J=1.7, 1H), 5.42 (dd, J=2.0, 3.0, 1H), 5.26 (d, J=1.6, 1H), 5.24-5.19 (m, 1H), 5.16 (d, J=1.6, 1H), 5.10 (s, 1.5H), 5.09-5.08 (m, 0.5H), 5.05-4.68 (m, 15H), 4.68-4.61 (m, 3H), 4.60-4.49 (m, 10H), 4.48-4.21 (m, 12H), 4.21-4.07 (m, 6H), 4.07-3.85 (m, 14H), 3.85-3.75 (m, 4H), 3.63 (m, 3H), 3.46 (m, 4H), 3.40-3.26 (m, 7H), 3.23-3.12 (m, 2H), 2.11 (s, 3H), 2.05 (s, 3H); ESI-MS (m/z):

[M+2(NH$_4$)]$^{2+}$ calculated for C$_{196}$H$_{210}$N$_2$O$_{40}$$^{2+}$, 1615.7; Found: 1615.5 as a dominant peak.

To a solution of pseudoheptasaccharide 36p (120 mg, 0.037 mmol) in THF (3 mL) a solution of NaOMe in MeOH (1.50 mL of 0.250 M, 0.375 mmol, freshly prepared from Na(s) and MeOH) was added at rt. The reaction was stirred at 50° C. for 18 h and neutralized with acid resin (methanol washed Amberlite IR-120). The reaction mixture was filtered through a short plug of silica gel, concentrated in vacuo and placed under high vacuum for 4 h. A solution of this crude product and BnBr (44.5 μL, 0.375 mmol) in DMF (4 mL) was cooled to 0° C. and NaH (60% in mineral oil, 15.0 mg, 0.375 mmol) was added. The reaction mixture was allowed to warm to rt. After 18 h at rt, the reaction mixture was transferred to a separatory funnel and carefully quenched by minimum amount of MeOH and water (10 mL). The reaction mixture was extracted with EtOAc (3×10 mL). The combined organic layer was washed with brine, dried over Na$_2$SO$_4$, and concentrated in vacuo. The crude product was purified by flash silica column chromatography (cyclohexane/EtOAc) to obtain the title compound 36 (118.7 mg, 97%, 2 steps) as a colorless syrup. R$_f$ 0.34 (cyclohexane/EtOAc=7:3); [α]$_D^{r.t.}$=+35.0 (c=1.0, CHCl$_3$); $^1$H NMR (300 MHz, CDCl$_3$) δ 7.46-7.03 (m, 115H), 5.49 (brs, 1H), 5.29-5.17 (m, 3H), 5.04-4.78 (m, 9H), 4.78-3.99 (m, 46H), 3.99-3.50 (m, 29H), 3.49-3.15 (m, 6H), 1.70 (brs, 1H); HRMS-MALDI (m/z): [M+Na]$^+$ calculated for C$_{203}$H$_{210}$O$_{36}$Na, 3246.4494; Found: 3246.4406.

General Procedures to Remove Allyl Protecting Group by the Ir Complex to Prepare Compounds 38-43:

Each oligosaccharide starting material (31-36) was coevaporated with toluene (3×) and placed under high vacuum for 4 h prior to the reaction. Under an argon atmosphere, a solution of Ir{(COD)[PH$_3$(C$_6$H$_5$)$_2$]$_2$}PF$_6$ (cat. i.e. 0.2 equiv.) in THF (distilled over sodium) was degassed by vacuum and gassed with H$_2$ (g) balloon (~5 cycles). The reaction was stirred under H$_2$ atmosphere at rt for 5 min before the solution was degassed by vacuum and gassed with argon (~5 cycles). To this reaction flask, a solution of an allyl protected compound (31-36, 1 equiv., ~0.05 mmol) in THF (1 mL) was added via syringe in one portion at rt. The reaction was stirred at rt for 2 h before concentrated in vacuo. The completed isomerization of the terminal allyl group was verified by $^1$H NMR. The crude product was treated with p-TsOH (0.1 equiv. for 31, 10 equiv. for 32-36) in a mixture of CH$_2$Cl$_2$ and MeOH (3:1, total volume=2.66 mL) for 12 h at rt. The reaction solution was diluted with EtOAc (20 mL), washed with saturated aqueous NaHCO$_3$ (3×) and brine, dried over Na$_2$SO$_4$ and concentrated in vacuo. The crude product was purified by flash silica column chromatography (cyclohexane/EtOAc) to obtain the title compounds 38 (quant.); 39 (71%); 40 (81%); 41 (79%); 42 (87%); or 43 (89%) as colorless syrup.

General Procedures for Phosphorylations to Prepare the Protected Phosphodiesters 45(a-g):

Each oligosaccharide (37-43) was combined with the 6-(S-benzyl)thiohexyl H-phosphonate 44, coevaporated with pyridine (3×) and placed under high vacuum for 4 h prior to the reaction. To a solution of an oligosaccharide backbone (37-43, ~0.03 mmol) and 44 (0.15 mmol) in pyridine (2 mL), PivCl (0.3 mmol) was added at rt. After 3 h at rt, iodine (0.21 mmol) in a mixture of pyridine and water (10:1, 300 μL total volume) was added to the reaction solution at rt and stirred for 1 h. The reaction mixture was diluted with CH$_2$Cl$_2$ (10 mL) and Na$_2$S$_2$O$_3$ (20 mL of 1 M) and extracted with CH$_2$Cl$_2$ (3×10 mL). The combined organic layer was dried over Na$_2$SO$_4$(s), concentrated in vacuo, purified by flash silica column chromatography (CH$_2$Cl$_2$/MeOH gradient, silica gel was neutralized with 1% NEt$_3$ in CH$_2$Cl$_2$ prior to use) and size exclusion column chromatography (Sephadex LH-20, MeOH/CH$_2$Cl$_2$/NEt$_3$=100:100:0.05) to obtain compounds 45(a-g) as a colorless syrup (90% to quant.)

General Procedures for Birch Reductions to Prepare PI and PIM$_1$-PIM$_6$:

At −78° C. (dry ice/acetone bath), ammonia was condensed into a solution of a phosphodiester 45 (~0.02 mmol) in a mixture of THF (25 mL) and t-BuOH (0.5 mL). Small pieces of Na(s) was added to the reaction to generate a stable dark blue solution for at least 30 min and MeOH was added to the reaction solution. Then, small pieces of Na(s) was again added to the reaction to generate a stable dark blue solution for at least 30 min and MeOH was added to the reaction solution. The reaction was allowed to slowly warm to rt by removing the dry ice/acetone bath and most of the remaining ammonia in the reaction solution was blown off by argon stream. The reaction solution was concentrated in vacuo, re-dissolved in water, neutralized with a small amount of acid resin (methanol washed Amberlite IR-120). The resin was filtered off and the mother liquor was concentrated in vacuo, re-dissolved in water, and extracted with CHCl$_3$ to remove the less polar partially debenzylated side products. The volume of the aqueous layer was decreased by lyophilzation and the aqueous solution was dialysed to afford the final product PI, PIM$_1$, PIM$_2$, PIM$_3$, PIM$_4$, PIM$_5$, or PIM$_6$.

PI: White solid (65%); $^1$H NMR (300 MHz, D$_2$O) δ 4.25 (t, J=2.7, 1 H), 4.01-3.83 (m, 3H), 3.81-3.47 (m, 4H), 3.33 (t, J=9.3, 1H), 2.81-2.74 (m, 0.2H), 2.42 (t, 1.8H), 1.74-1.51 (m, 4H), 1.49-1.34 (m, 4H); $^{31}$P NMR (121 MHz, CDCl$_3$) δ 0.79; ESI-MS (m/z): [M−H]$^−$ calculated for C$_{12}$H$_{24}$O$_6$PS$^−$, 375.0; Found: 374.6 as a dominant peak.

PIM$_1$: White solid (43%); $^1$H NMR (300 MHz, D$_2$O) δ 5.13 (d, J=1.5, 1H), 4.32-4.25 (m, 1H), 4.13-4.06 (m, 1H), 4.04-3.53 (m, 12H), 3.31 (t, J=8.8, 1H), 2.88-2.68 (m, 0.5H), 2.54 (t, J=7.1, 1.5H), 1.76-1.51 (m, 4H), 1.50-1.29 (m, 4H); $^{13}$C NMR (75 MHz, D$_2$O) δ 101.69, 79.27, 76.46, 76.41, 74.43, 72.97, 72.69, 72.08, 72.03, 70.60, 70.37, 70.25, 66.87, 66.68, 66.63, 61.12, 38.42, 33.18, 30.02, 29.97, 29.96, 28.53, 27.51, 27.35, 24.77, 24.60, 23.93; $^{31}$P NMR (121 MHz, CDCl$_3$) δ 0.86; HRMS-ESI (m/z): [M−H]$^−$ calculated for C$_{13}$H$_{34}$O$_{14}$PS$^{1−}$, 537.1412; Found: 537.1403.

PIM$_2$: White solid (56%); $^1$H NMR (500 MHz, D$_2$O) δ 5.04 (s, 1H), 5.02 (s, 1H), 4.19 (s, 1H), 4.06-3.42 (m, 20H), 3.23 (t, J=9.2, 1 H), 2.65 (t, J=7.2, 2H), 1.65-1.45 (m, 4H), 1.44-1.22 (m, 4H); $^{13}$C NMR (125 MHz, D$_2$O) δ 101.62, 101.60, 78.96, 78.34, 78.29, 76.68, 73.26, 72.99, 72.84, 70.61, 70.41, 70.25, 70.12, 66.89, 66.79, 66.53, 61.14, 60.92, 38.41, 30.17, 30.12, 28.54, 27.48, 24.85; $^{31}$P NMR (121 MHz, CDCl$_3$) δ 0.48; HRMS-ESI (m/z): [MS−SM−2H]$^{2−}$ calculated for C$_{48}$H$_{86}$O$_{38}$P$_2$S$_2$$^{2−}$, 698.1863; Found: 698.1862.

PIM$_3$: White solid (91%); $^1$H NMR (600 MHz, D$_2$O) δ 5.15 (s, 1H), 5.10 (s, 1H), 4.90 (s, 1H), 4.30 (d, J=1.9, 1H), 4.21-4.04 (m, 4H), 4.03-3.90 (m, 5H), 3.90-3.72 (m, 10H), 3.64 (m, 7H), 3.36 (t, J=9.1, 1 H), 2.77 (t, J=7.2, 1.7H), 2.54 (t, J=7.1, 0.3H), 1.80-1.58 (m, 4H), 1.42 (brs, 4H); $^{13}$C NMR (150 MHz, D$_2$O) δ 104.27, 104.12, 102.26, 81.37, 81.10, 81.06, 79.29, 79.26, 75.68, 75.51, 75.48, 75.43, 73.70, 73.36, 73.31, 73.15, 72.93, 72.73, 72.59, 69.53, 69.39, 69.36, 69.33, 69.28, 69.24, 68.33, 63.69, 63.66, 40.95, 32.60, 32.56, 32.45, 31.02, 30.12, 29.93, 27.32, 27.15; $^{31}$P NMR (121 MHz, CDCl$_3$) δ 0.33; HRMS-ESI (m/z): [M−H+2Na]$^+$ calculated for C$_{30}$H$_{54}$O$_{24}$PSNa$_2$$^+$, 907.2253; Found: 907.2244.

PIM$_4$: White solid (65%); $^1$H NMR (600 MHz, D$_2$O) δ 5.17 (d, J=1.8, 1H), 5.12 (d, J=1.5, 1H), 4.90 (d, J=1.6, 1H), 4.90 (d, J=1.6, 1H), 4.35-4.28 (m, 1H), 4.22-4.16 (m, 1H), 4.15 (dd, J=1.7, 3.2, 1H), 4.12 (dd, J=1.9, 3.3, 1H), 4.10-4.06 (m, 1H), 4.03-3.89 (m, 8H), 3.89-3.73 (m, 13H), 3.73-3.55 (m, 8H), 3.37 (td, J=3.3, 9.2, 1H), 2.84-2.72 (m, 1.5H), 2.56 (t, J=7.2, 0.5H), 1.80-1.56 (m, 4H), 1.52-1.36 (m, 4H); $^{13}$C NMR (150 MHz, D$_2$O) δ 104.26, 104.08, 102.22, 102.07, 81.40, 81.36, 81.02, 80.97, 79.09, 79.05, 75.65, 75.46, 75.42, 73.56, 73.47, 73.38, 73.26, 73.09, 72.89, 72.71, 72.69, 72.64, 72.56, 69.47, 69.36, 69.35, 69.22, 69.00, 68.96, 68.38, 68.09, 63.66, 63.61, 40.88, 35.63, 32.62, 32.58, 31.01, 29.94, 29.78, 27.31, 27.14, 26.40; $^{31}$P NMR (121 MHz, CDCl$_3$) δ −0.49, −0.48; HRMS-ESI (m/z): [M−H]$^-$ calculated for C$_{36}$H$_{64}$O$_{29}$PS$^-$, 1023.2997; Found: 1023.2990.

PIM$_5$: White solid (88%); $^1$H NMR (500 MHz, D$_2$O) δ 5.05 (s, 1H), 5.02 (s, 1H), 5.01 (s, 1H), 4.92 (s, 1H), 4.79 (s, 1H), 4.20 (s, 1H), 4.11-3.44 (m, 39H), 3.26 (t, J=9.1, 1H), 2.67 (t, J=7.2, 1.5H), 2.41 (t, J=7.3, 0.4H), 1.66-1.47 (m, 4H), 1.32 (m, 4H); $^{13}$C NMR (125 MHz, D$_2$O) δ 102.48, 101.78, 101.61, 99.80, 98.33, 78.93, 78.48, 78.43, 76.64, 76.59, 73.44, 73.17, 72.99, 71.33, 71.05, 71.00, 70.91, 70.62, 70.56, 70.45, 70.42, 70.25, 70.20, 70.18, 70.09, 67.19, 67.15, 66.87, 66.84, 66.73, 66.53, 66.49, 66.20, 65.61, 61.37, 61.18, 61.14, 38.40, 33.17, 30.16, 30.11, 28.54, 27.47, 27.31, 24.85, 24.67, 23.94; $^{31}$P NMR (121 MHz, CDCl$_3$) δ 0.38, 0.33; HRMS-ESI (m/z): [M−H+2Na]$^+$ calculated for C$_{42}$H$_{74}$O$_{34}$PSNa$_2^+$, 1231.3322; Found: 1231.3310.

PIM$_6$: White solid (52%); $^1$H NMR (500 MHz, D$_2$O) δ 5.16 (d, J=1.1, 1H), 5.04 (s, 1H), 4.99 (s, 1H), 4.98 (s, 1H), 4.91 (d, J=1.4, 1H), 4.77 (s, 1H), 4.18 (s, 1H), 4.10-3.91 (m, 5H), 3.90-3.40 (m, 37H), 3.24 (t, J=9.1, 1 H), 2.65 (t, J=7.3, 1 H), 2.43 (t, J=7.3, 0.3; H), 2.27-2.21 (m, 0.15H), 1.69-1.36 (m, 4H), 1.30 (s, 4H); $^{13}$C NMR (125 MHz, D$_2$O) δ 102.43, 101.78, 101.61, 100.85, 99.81, 98.41, 78.99, 78.94, 78.90, 78.69, 78.49, 78.44, 76.65, 76.60, 73.46, 73.18, 72.98, 71.39, 71.01, 70.93, 70.62, 70.56, 70.46, 70.42, 70.24, 70.20, 70.17, 70.09, 67.31, 67.17, 67.06, 66.87, 66.82, 66.71, 66.54, 66.49, 66.23, 65.57, 61.35, 61.29, 61.16, 61.14, 38.40, 33.17, 30.16, 30.11, 28.54, 27.48, 27.31, 24.84, 24.67, 23.93; $^{31}$P NMR (121 MHz, CDCl$_3$) δ −0.50, −0.47; HRMS-ESI (m/z): [M−H]$^-$ calculated for C$_{48}$H$_{84}$O$_{39}$PS$^-$, 1347.4054; Found: 1347.4049.

Immunization of Mice and Detection of Anti-KLH Antibody Levels in Sera:

Preparation of keyhole limpet hemocyanin (KLH) in complete/incomplete Freund's adjuvant was performed by mixing KLH with Freund's adjuvant in a 1:1 volume ratio. For coupling of PIM$_6$ to KLH, PIM$_6$ was incubated with Tris(2-carboxyethyl)phosphine HCl (TCEP) (to reduce disulfide bonds) in equal molar ratio for one hour at rt. A molar excess of PIM$_6$ was then coupled to KLH using the Imject® Maleimide Activated mcKLH Kit (Pierce, Rockford, Ill.) according to manufacturer's instructions. PIM$_6$-KLH conjugate was purified by gel filtration chromatography and the protein concentration in the eluate was determined by measuring the absorption at a wavelength of 280 nm.

Female C57BL/6 mice (6-8 weeks old) were housed in the HCl rodent center, ETH Zurich, and were provided food and water ad libitum. On day 0 four mice per group were s.c. immunized with KLH alone (group 1), KLH in complete Freund's adjuvant (group 2), KLH with alum (group 3), KLH with CpG (group 4) or KLH coupled to PIM$_6$ (group 5). On day 10, mice received a boost immunization with KLH alone (group 1), KLH in incomplete Freund's adjuvant (group 2), KLH with alum (group 3), KLH with CpG (group 4) or KLH coupled to PIM$_6$ (group 5). The amount of KLH was adjusted to 50 µg per mouse and immunization. On day 17, blood was taken from the saphenous vein and serum was separated from the clotted blood by centrifugation. All animal experiments were in accordance with local Animal Ethics Committee regulations.

Figure 3:
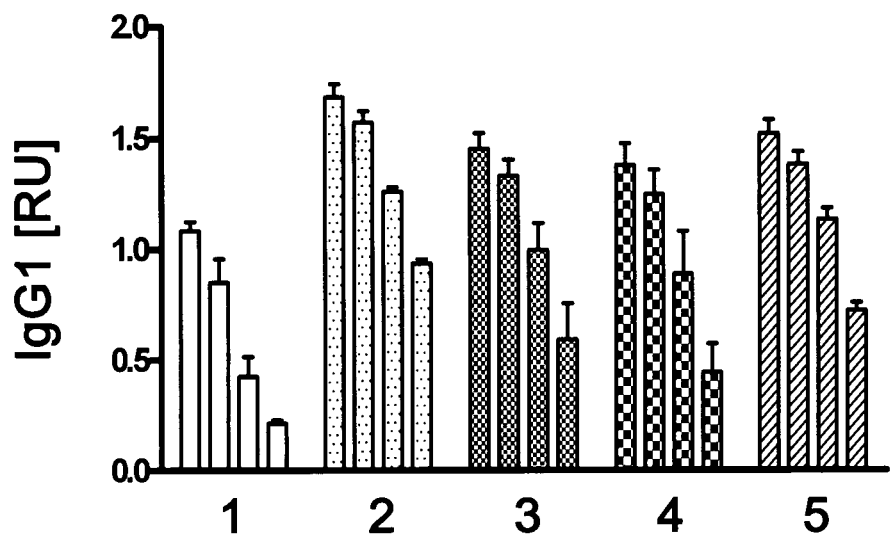
Figure 3:
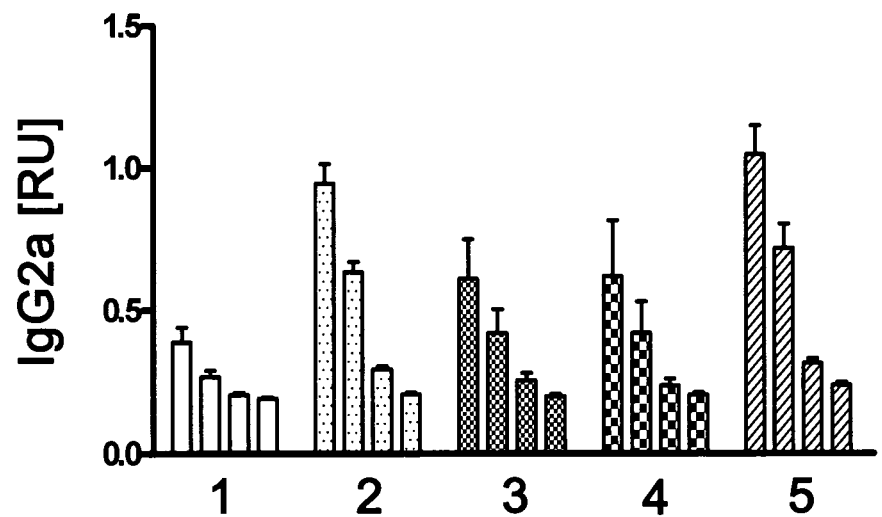

Levels of anti-KLH antibodies in sera of immunized mice were measured by ELISA: Microlon microplates (Greiner, Frickenhausen, Germany) were coated with 10 µg/mL KLH in 0.05 M Na$_2$CO$_3$ buffer (pH 9.6) at 4° C. overnight. After blocking with 1% BSA/PBS for two hours at rt and washing with 0.05% Tween-20/PBS plates were incubated with serial dilutions of sera (diluted in 0.1% BSA/PBS) for two hours. Plates were then washed three times with 0.05% Tween-20/PBS and incubated with HRP-conjugated goat-anti-mouse IgG+A+M antibody in a dilution of 1:1000 (Invitrogen, Basel, Switzerland). Detection was performed by using the 3,3',5,5'-Tetramethylbenzidine Liquid Substrate System (Sigma-Aldrich, Buchs, Switzerland) according to manufacturer's instructions. Results are shown in FIGS. 2 and 3.

T Cell Proliferation and ELISpot Analysis.

On day 20 after the first immunization, mice were sacrificed and spleens were removed. RBCs were lysed by adding hypotonic ammonium chloride solution. Single cell suspensions were cultivated at 2×10$^5$ cells per well in 96-well plates for 24 h in the presence of medium or KLH (10 µg/ml) for restimulation of T cells ex vivo. Proliferation of spleen cells was measured using the CellTiter 96® AQueous One Solution Cell Proliferation Assay (Promega, Madison, Wis.) according to the manufacturer's instructions. Results are shown in FIG. 4.

ELISpot analysis was performed on day 20 after the first immunization using a mouse IFN-γ ELISpot Kit (R&D Systems, Minneapolis, Minn.). Briefly, 2×10$^5$ spleen cells per well were stimulated for 24 h in the presence of medium, KLH (10 µg/ml) or the T cell mitogen concanavalin A (ConA, 10 µg/ml). Spot development was performed according to the manufacturer's instructions and the number of spots was determined using an ELISpot reader (AID, Straβberg, Germany). Results are shown in FIG. 5.

Statistical Analysis.

Statistical analyses were performed applying unpaired Student's t-test. All statistical analyses were performed with the Prism software (Graph Pad Software, San Diego, Calif.).

The invention claimed is:

1. A compound of formula (I)

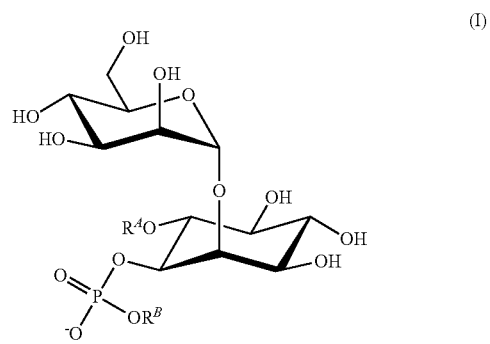

wherein

R$^A$ is H, a residue of formula (II), (III), (IV), (V) or (VI)

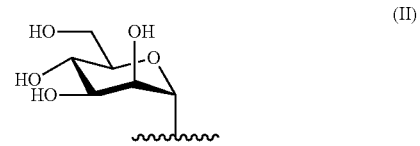

-continued

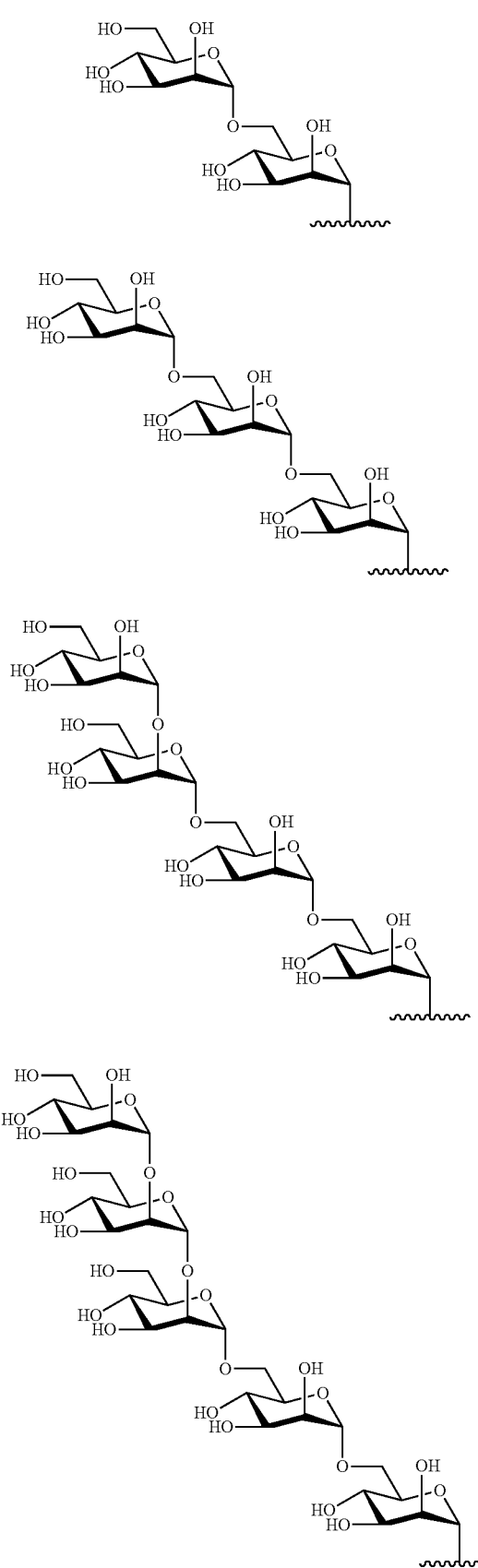

and $R^B$ is —$(CH_2)_n$—X wherein n is from 2 to 10 or —$(CH_2CH_2O)_mCH_2CH_2X$ wherein m is from 1 to 5, and X is a reactive functional group, a protein, a fluorescent probe or a solid phase.

2. The compound according to claim 1 wherein $R^B$ is —$(CH_2)_n$—X.

3. The compound according to claim 2 wherein $R^B$ is —$(CH_2)_m$—X wherein n is 4, 5 or 6.

4. The compound according to claim 1 wherein $R^B$ is —$(CH_2CH_2O)_mCH_2CH_2X$ wherein m is from 1 to 5.

5. The compound according to claim 1 wherein X is a functional group selected from the group consisting of a sulfhydryl group (—SH), a maleimido function of formula (VII)

an amino group, and an optionally activated carboxyl group.

6. The compound according to claim 5 wherein X is the sulfhydryl group.

7. The compound according to claim 1 wherein X is a protein.

8. The compound according to claim 1 wherein X is a fluorescent probe.

9. The compound according to claim 1 wherein X is a solid phase.

10. The compound according to claim 1 wherein $R^B$ is —$(CH_2)_n$—X, n is 6 and X is a sulfhydryl group.

11. The compound according to claim 10 of formula

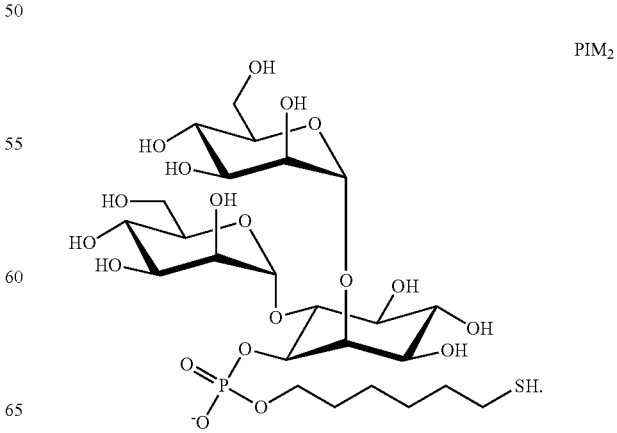

12. The compound according to claim 10 of formula
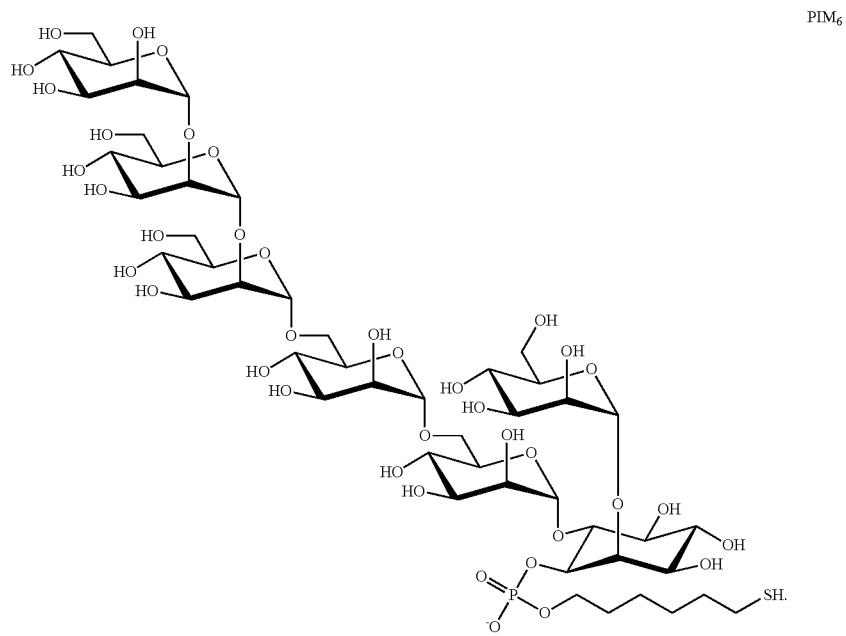
PIM₆
13. A vaccine comprising a compound of formula (I) according to claim 1 wherein X is a carrier protein or an antigen.
* * * * *